US007052488B2

(12) United States Patent
Uhland

(10) Patent No.: US 7,052,488 B2
(45) Date of Patent: May 30, 2006

(54) IMPLANTABLE DRUG DELIVERY DEVICE

(75) Inventor: Scott A. Uhland, Somerville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/637,319

(22) Filed: Aug. 8, 2003

(65) Prior Publication Data
US 2004/0034332 A1 Feb. 19, 2004

Related U.S. Application Data

(63) Continuation of application No. 10/314,838, filed on Dec. 9, 2002, now Pat. No. 6,656,162, which is a continuation of application No. 09/715,493, filed on Nov. 17, 2000, now Pat. No. 6,491,666.

(60) Provisional application No. 60/166,370, filed on Nov. 17, 1999.

(51) Int. Cl.
A61K 9/11 (2006.01)
A61M 37/00 (2006.01)

(52) U.S. Cl. ................. 604/891.1; 604/288.01

(58) Field of Classification Search ......... 604/890.1, 604/501, 502, 891.1, 892.1, 288.01, 288.04, 604/131; 216/2; 424/422–424
See application file for complete search history.

(56) References Cited

U.S. PATENT DOCUMENTS

| 3,692,027 | A | 9/1972 | Ellinwood, Jr. |
| 3,952,741 | A | 4/1976 | Baker |
| 4,003,379 | A | 1/1977 | Ellinwood, Jr. |
| 4,146,029 | A | 3/1979 | Ellinwood, Jr. |
| 4,360,019 | A | 11/1982 | Portner et al. |
| 4,507,115 | A | 3/1985 | Kambara et al. |
| 4,585,652 | A | 4/1986 | Miller et al. |
| 4,793,825 | A | 12/1988 | Benjamin et al. |
| 5,167,625 | A | 12/1992 | Jacobsen et al. |
| 5,170,801 | A | 12/1992 | Casper et al. |
| 5,196,002 | A | 3/1993 | Hanover et al. |
| 5,200,051 | A | 4/1993 | Cozzette et al. |
| 5,252,294 | A | 10/1993 | Kroy et al. |
| 5,318,557 | A | 6/1994 | Gross |
| 5,366,454 | A | 11/1994 | Currie et al. |
| 5,368,588 | A | 11/1994 | Bettinger |
| 5,368,704 | A | 11/1994 | Madou et al. |

(Continued)

FOREIGN PATENT DOCUMENTS

DE 197 16 683 6/1998

(Continued)

OTHER PUBLICATIONS

Low, et al., "Microactuators Towards Microvalves for Responsive Controlled Drug Delivery," *Sensors & Actuators B* 67: 149-60 (2000).

(Continued)

Primary Examiner—William E Tapolcai
(74) Attorney, Agent, or Firm—Jones Day

(57) ABSTRACT

Implantable devices for controlled delivery of a drug are provided which include a substrate; at least two reservoirs in the substrate, each reservoir having an opening; at least one therapeutic agent in each of the reservoirs; a reservoir cap sealing each opening; a mechanical rupturing mechanism which moves into contact with and ruptures the reservoir cap to permit release the therapeutic agent from the reservoir through the opening; and a mixing chamber adjacent the reservoirs, wherein upon release of the therapeutic agent from at least one of the reservoirs, the therapeutic agent is combined with a carrier fluid in the mixing chamber and then transported to a delivery site in a human or animal.

14 Claims, 13 Drawing Sheets

U.S. PATENT DOCUMENTS

| | | | |
|---|---|---|---|
| 5,429,822 | A | 7/1995 | Gresser et al. |
| 5,443,508 | A | 8/1995 | Giampapa |
| 5,547,470 | A | 8/1996 | Johnson et al. |
| 5,797,898 | A | 8/1998 | Santini et al. |
| 5,798,042 | A | 8/1998 | Chu et al. |
| 5,824,049 | A | 10/1998 | Ragheb et al. |
| 5,891,108 | A | 4/1999 | Leone et al. |
| 5,948,255 | A | 9/1999 | Keller et al. |
| 5,962,081 | A | 10/1999 | Öhman et al. |
| 5,972,027 | A | 10/1999 | Johnson |
| 5,989,445 | A | 11/1999 | Wise et al. |
| 6,071,305 | A | 6/2000 | Brown et al. |
| 6,096,070 | A | 8/2000 | Ragheb et al. |
| 6,114,658 | A | 9/2000 | Roth et al. |
| 6,123,861 | A | 9/2000 | Santini et al. |
| 6,241,762 | B1 | 6/2001 | Shanley |
| 6,273,908 | B1 | 8/2001 | Ndondo-Lay |
| 6,273,913 | B1 | 8/2001 | Wright et al. |
| 6,287,628 | B1 | 9/2001 | Hossainy et al. |
| 6,395,326 | B1 | 5/2002 | Castro et al. |
| 6,491,666 | B1 | 12/2002 | Santini et al. |
| 6,558,422 | B1 | 5/2003 | Baker et al. |
| 6,638,302 | B1 | 10/2003 | Curcio et al. |
| 6,662,044 | B1 * | 12/2003 | Crawford et al. ............ 604/20 |
| 6,709,379 | B1 | 3/2004 | Brandau et al. |
| 6,783,543 | B1 | 8/2004 | Jang |
| 2002/0038146 | A1 | 3/2002 | Harry |
| 2003/0069560 | A1 | 4/2003 | Adamis et al. |

FOREIGN PATENT DOCUMENTS

| | | |
|---|---|---|
| EP | 1 222 941 A2 | 7/2002 |
| WO | 01/12157 | 2/2001 |
| WO | 02/32347 A2 | 4/2002 |

OTHER PUBLICATIONS

Madou & Florkey, "From Batch to Continuous Manufacturing of Microbiomedical Devices," *Chem. Rev., 100:* 2679-92 (2000).

Madou, *Fundamentals of Microfabrication,* pp. 468-512 (CRC Press 1997).

Madou & He, "Exploitation of a Novel Artificial Muscle for Controlled Drug Delivery," pp. 495-497 (1999).

Surbled, et al., "Shape Memory Alloys for Micromembranes Actuation," *SPIE. 3825:* 63-70 (1999).

Surbled, et al., et al., "Array of Shape Memory Alloy One-Shot Micro-Valves for Drug Delivery," MME '99, Gif sur Yvette, France (Sep. 27-28, 1999).

Tierney, et al. "New Electrorelease Systems Based on Microporous Membranes," *J. Electrochem, Soc., 137:*3789-3793 (1990).

* cited by examiner

| | |
|---|---|
| ☐ | INSULATOR/ETCH MASK MATERIAL |
| ▨ | ANODE AND CATHODE MATERIAL |
| ▦ | INSULATOR OVERLAYER |
| ▨ | MOLECULE (SOLID, LIQUID, OR GEL FORM) AND RELEASE SYSTEM |
| ▨ | CARRIER LIQUID |

T1 < T2 < T3
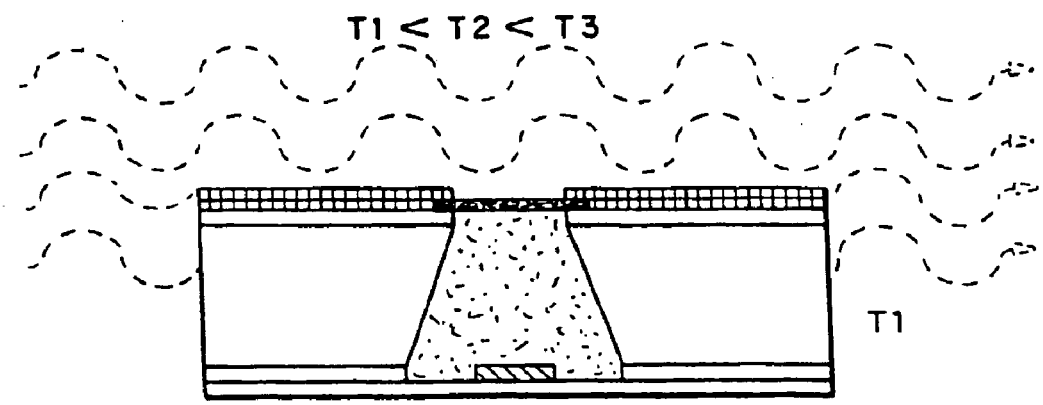
FIG. 4A
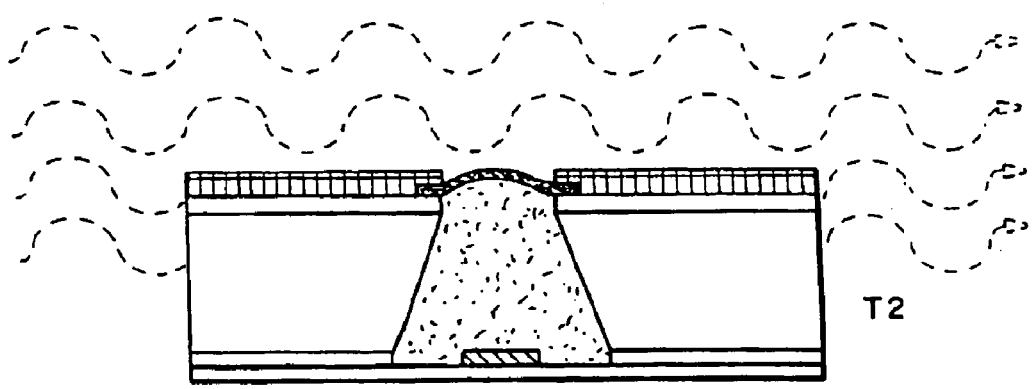
FIG. 4B
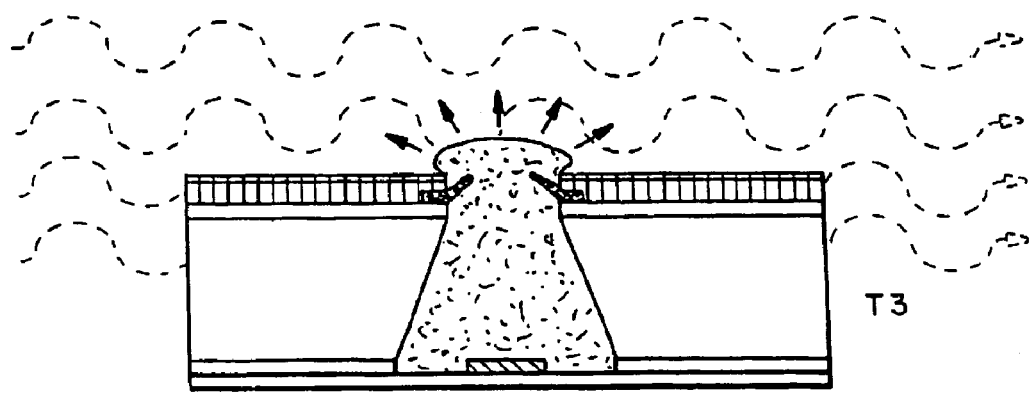
FIG. 4C
 RESISTOR
 INSULATOR/ETCH MASK MATERIAL
 CAP MATERIAL
 INSULATOR OVERLAYER
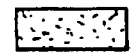 MOLECULE (SOLID, LIQUID, OR GAS FORM) AND RELEASE SYSTEM

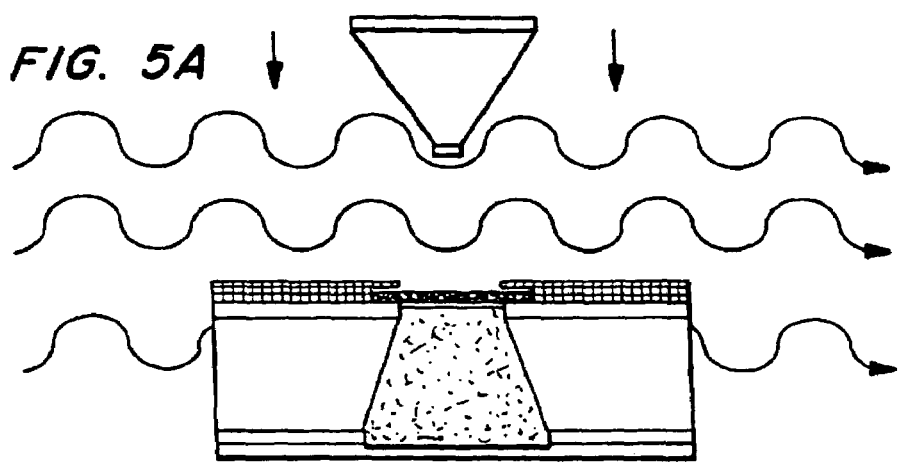
FIG. 5A
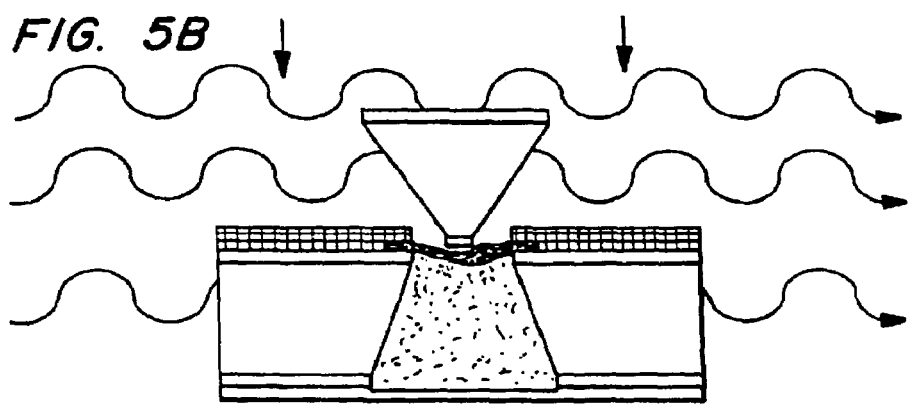
FIG. 5B
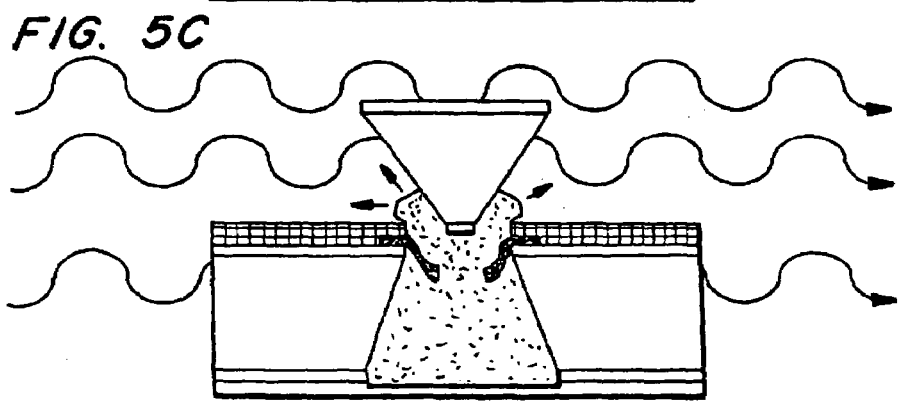
FIG. 5C
 RESISTOR
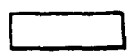 INSULATOR / ETCH MASK MATERIAL
 CAP MATERIAL
 INSULATOR OVERLAYER
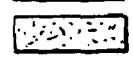 MOLECULE (SOLID, LIQUID, OR GAS FORM) AND RELEASE SYSTEM

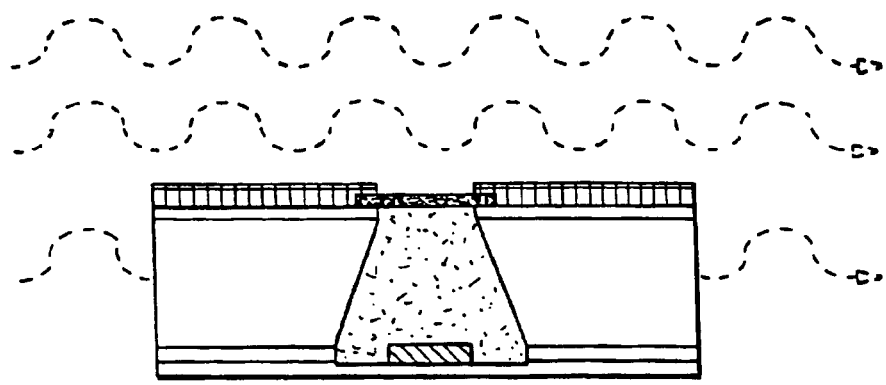
FIG. 6A
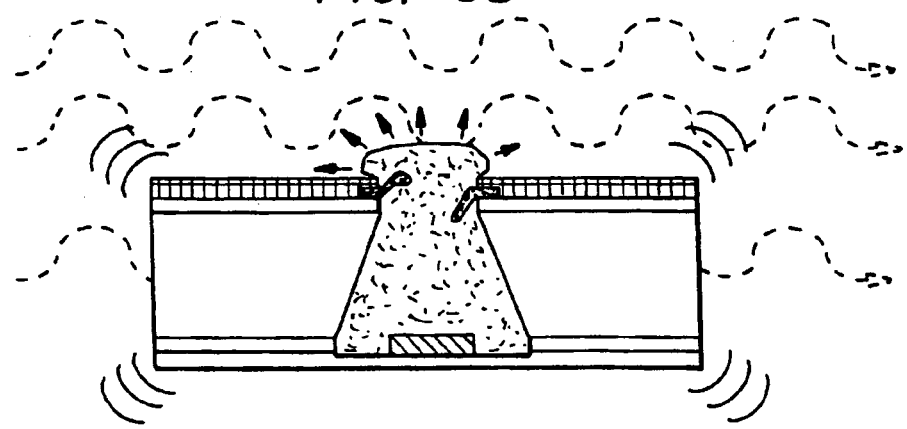
FIG. 6B
| | |
|---|---|
| 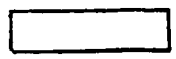 | INSULATOR / ETCH MASK MATERIAL |
|  | CAP MATERIAL |
|  | INSULATOR OVERLAYER |
| 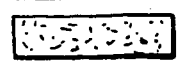 | MOLECULE (SOLID, LIQUID, OR GAS FORM) AND RELEASE SYSTEM |
|  | PIEZOELECTRIC MATERIAL |

FIG. 7A
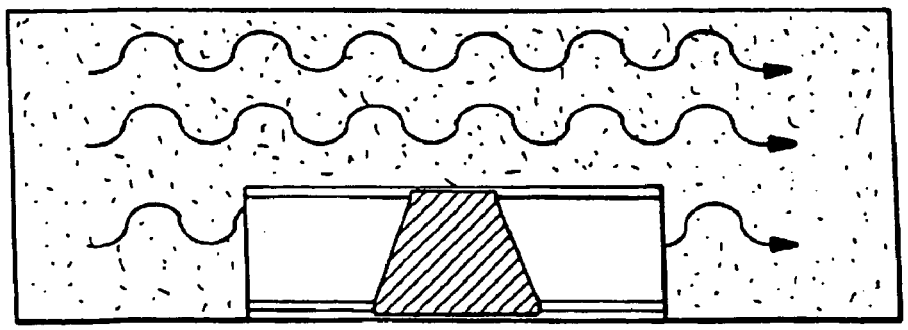
FIG. 7B
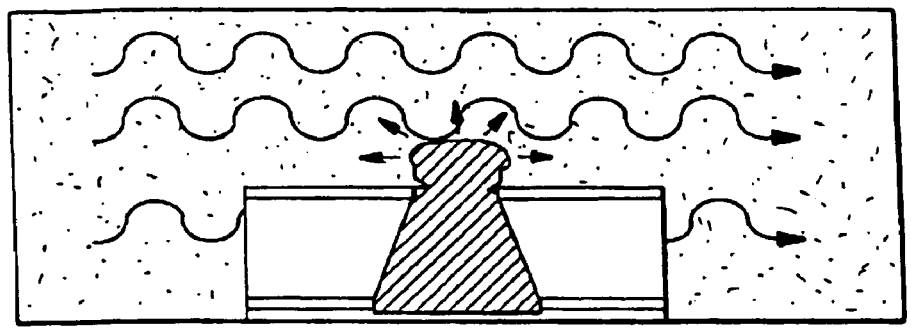
FIG. 7C
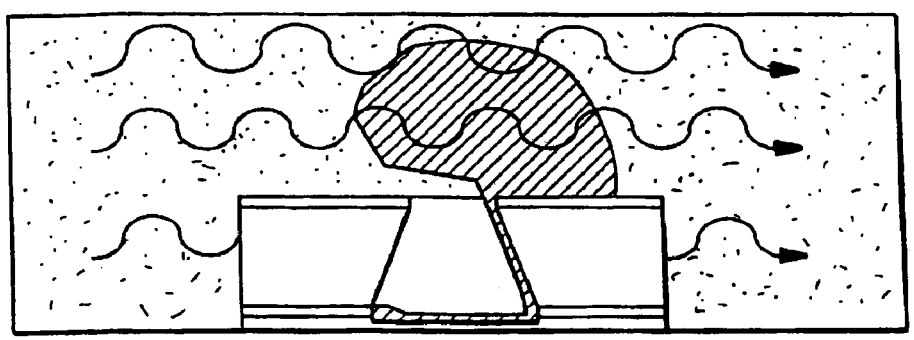
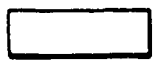 INSULATOR / ETCH MATERIAL
 MOLECULE (SOLID, LIQUID, OR GEL FORM) AND DEGRADABLE RELEASE SYSTEM
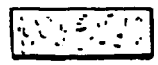 CARRIER LIQUID

ARRAY OF MICROCHIPS ON THE STENT'S INSIDE SURFACE

SQUARE APERTURE

STENT

VERTICAL CROSS-SECTIONAL VIEW

STENT WALL

ARRAY OF MICROCHIPS

SQUARE APERTURE

VERTICAL CROSS-SECTIONAL VIEW

STENT WALL

SQUARE APERTURE

ARRAY OF MICROCHIPS

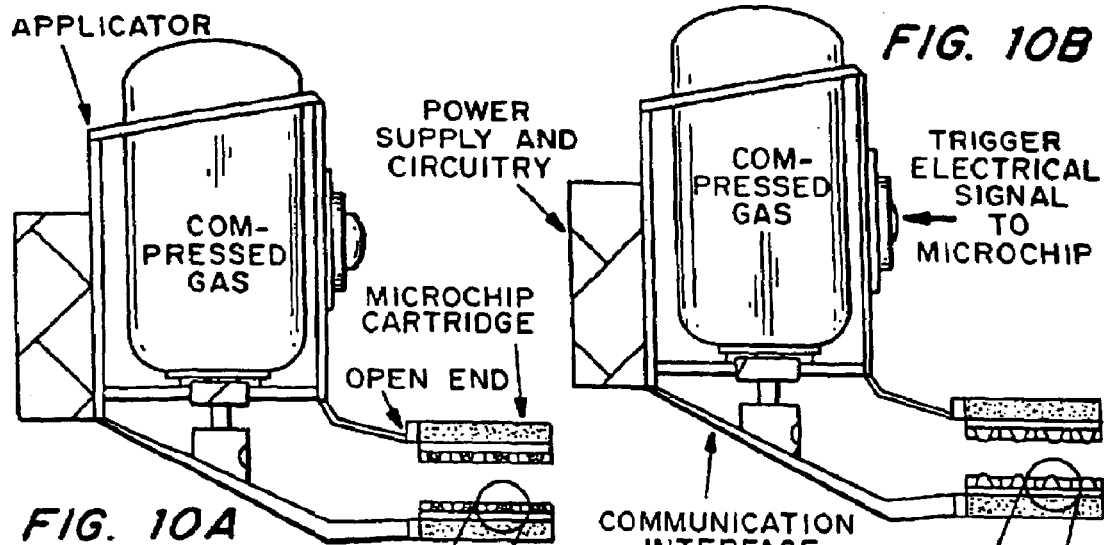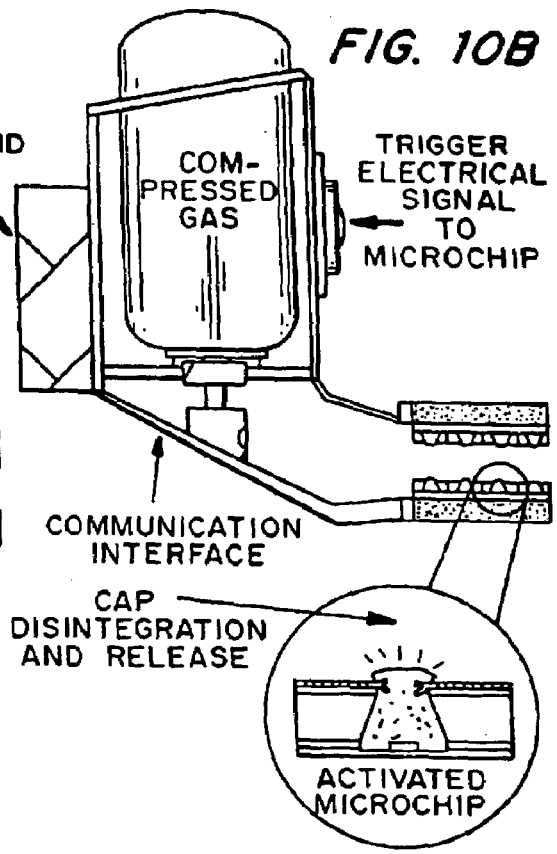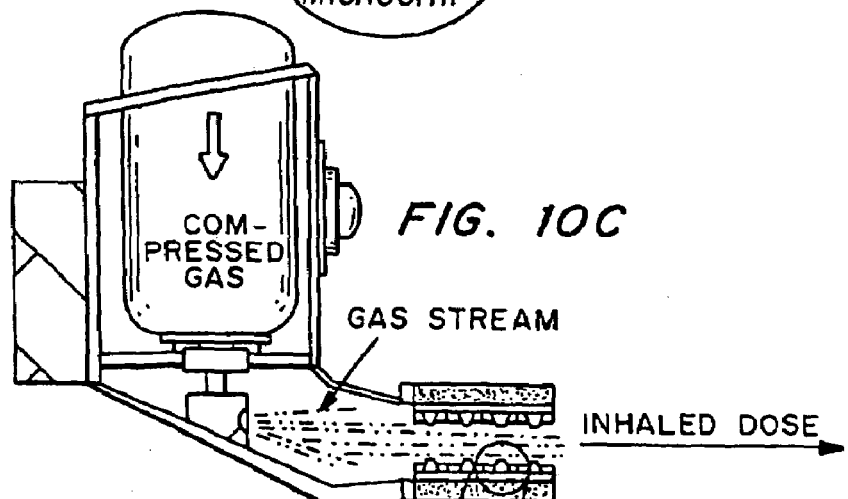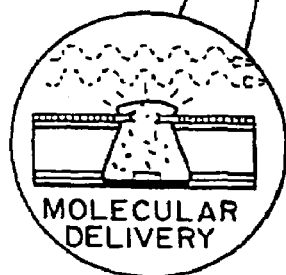

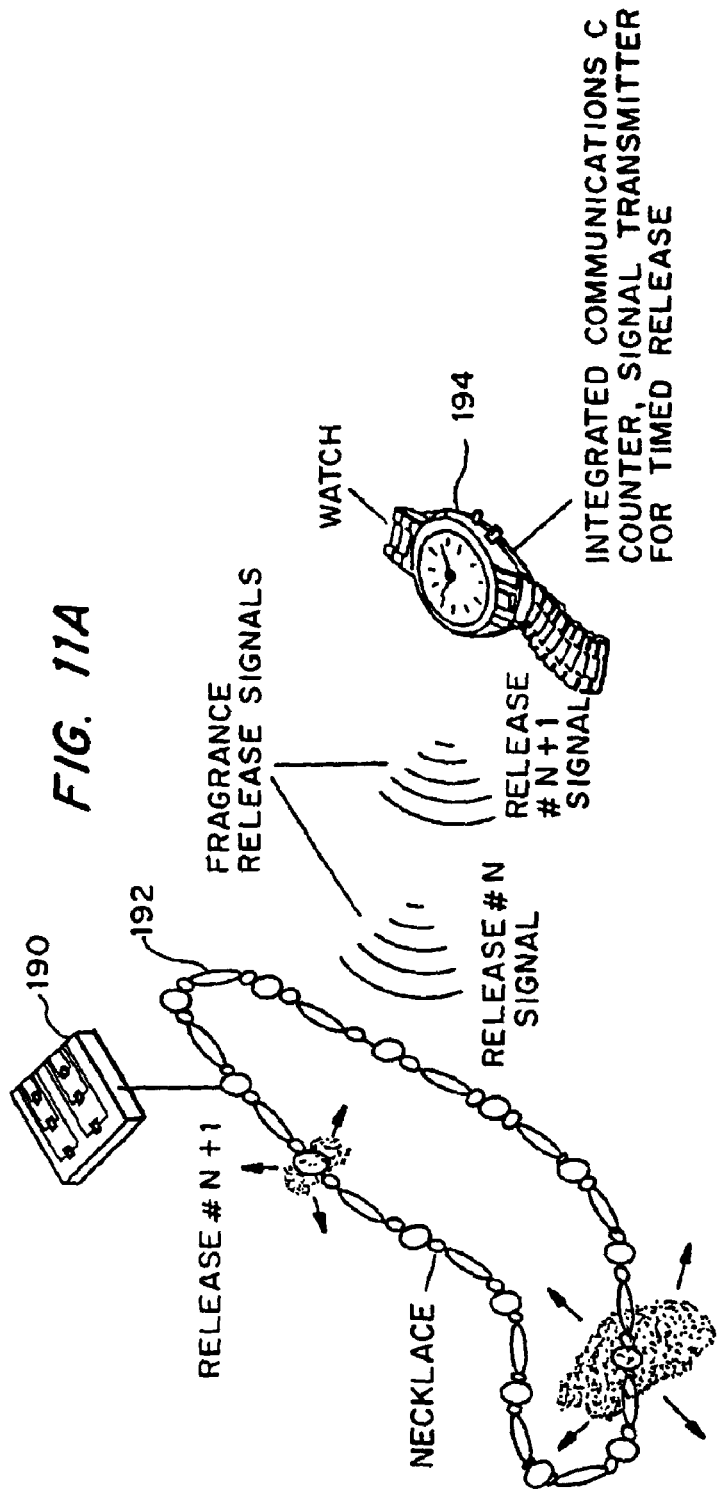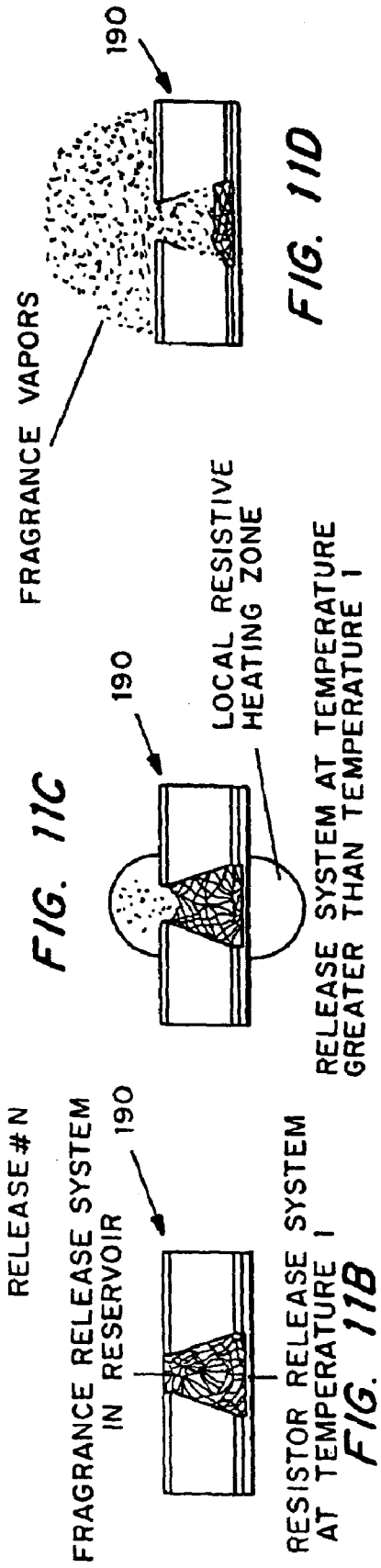

IMPLANTABLE DRUG DELIVERY DEVICE

CROSS-REFERENCE TO RELATED APPLICATIONS

This is a continuation U.S. application Ser. No. 10/314,838, filed Dec. 9, 2002, now U.S. Pat. No. 6,656,162, which is a continuation of U.S. application Ser. No. 09/715,493, filed Nov. 17, 2000, now U.S. Pat. No. 6,491,666. Application Ser. No. 09/715,493 claims benefit of U.S. Provisional Application No. 60/166,370, filed Nov. 17, 1999. All of these applications are incorporated herein by reference in their entirety.

BACKGROUND OF THE INVENTION

This invention relates generally to miniaturized devices for controlled delivery of chemical molecules into a carrier fluid.

Accurate delivery of small, precise quantities of one or more chemicals into a carrier fluid are of great importance in many different fields of science and industry. Examples in medicine include the delivery of drugs to patients using intravenous methods, by pulmonary or inhalation methods, or by the release of drugs from vascular stent devices. Examples in diagnostics include releasing reagents into fluids to conduct DNA or genetic analyses, combinatorial chemistry, or the detection of a specific molecule in an environmental sample. Other applications involving the delivery of chemicals into a carrier fluid include the release of fragrances and therapeutic aromas from devices into air and the release of flavoring agents into a liquid to produce beverage products.

U.S. Pat. No. 5,547,470 to Johnson, et al., discloses automated devices for intravenous drug delivery in which plural pumping channels independently infuse drugs and fluid. These devices and delivery methods require that the drugs be carefully pre-mixed and stored in a liquid form. A liquid form can, however, reduce the stability of some drugs and therefore can cause undesirable variability of the drug concentration. It would be desirable to more accurately and reliably measure the amount of drug introduced into the intravenous carrier fluid, as well as to store the drug in a more stable form, for example as a solid.

U.S. Pat. No. 5,972,027 to Johnson discloses the use of porous metallic stents as vascular drug delivery devices. The devices reportedly deliver a drug from the porous structure of the stent to the surrounding tissue. Such devices, however, are limited in the number of drugs that they can deliver and are severely limited in the control of both the rate and time of drug delivery, as the delivery rate is governed by the porous structure. It would be advantageous to provide active and more precise control over the time and rate of delivery of a one or more of variety of drugs from the stents into, for example, the bloodstream passing through the implanted stent.

Microchip delivery devices, described in U.S. Pat. No. 5,797,898 and U.S. Pat. No. 6,123,861 to Santini et al., provide a means to control both the rate and time of release of a variety of molecules, such as drugs, in either a continuous or pulsatile manner. The devices further provide a means for storing the chemicals in their most stable form. These patents describe, for example, implanting the microchip devices by themselves into a patient for delivery of drug. It would be advantageous, however, to adapt the precise control of molecule release provided by these microchip devices into a variety of other applications.

SUMMARY OF THE INVENTION

Apparatus and methods are provided for the delivery of molecules to a site via a carrier fluid. The apparatus include microchip devices which have reservoirs containing the molecules for release. The apparatus and methods provide for active or passive controlled release of the molecules. The microchip devices include (1) a substrate, (2) at least two reservoirs in the substrate containing the molecules for release, and (3) a reservoir cap positioned on, or within a portion of, the reservoir and over the molecules, so that the molecules are controllably released from the device by diffusion through or upon disintegration or rupture of the reservoir caps. Each of the reservoirs of a single microchip can contain different molecules and/or different amounts and concentrations, which can be released independently. The filled reservoirs can be capped with materials that passively or actively disintegrate. Passive release reservoir caps can be fabricated using materials that allow the molecules to diffuse passively out of the reservoir over time. Active release reservoir caps can be fabricated using materials that disintegrate upon application of electrical, mechanical, or thermal energy. Release from an active device can be controlled by a preprogrammed microprocessor, remote control, or by biosensors.

The carrier fluids into which the molecules are released can be, for example, environments such as intravenous infusions, beverage mixtures, vascular fluids, and gaseous phases. In a preferred embodiment, the microchip device releases molecules that are contained within the reservoirs into a fluid that is delivered to a patient intravenously.

In another embodiment, the microchip device is integrated into a stent for the delivery of drugs, such as anti-restenosis drugs or such as pravastatin or other hypertension medications.

In yet another embodiment, the microchip delivers molecules, which can be in the form of, but not limited to aerosols, vapors, gases, or a mixture thereof, into a stream for either therapeutic or aesthetic purposes.

In general, the microchip provides a method for storing molecular species in their most stable form, which can be a solid, liquid, gel, or gas. Upon either passive or active reservoir opening, the one or more types of molecules are released into the carrier fluid in either a pulsatile or continuous manner. These methods will provide fine control over the amount of the molecules delivered as well as the time and rate at which delivery occurs. Additionally, the molecular delivery device will extend the shelf-life (i.e. stability) of the molecules offering new potential applications.

BRIEF DESCRIPTION OF THE DRAWINGS

FIGS. 4a–c are cross-sectional views showing the active release of molecules into a carrier gas.

FIGS. 5a–c are cross-sectional views showing a reservoir cap of a microchip device being ruptured by direct application of a mechanical force.

FIGS. 6a–b are cross-sectional views showing a reservoir cap of a microchip device being ruptured by application of ultrasound.

FIGS. 7a–c are cross-sectional views showing the passive release of molecules from a microchip device into a carrier liquid.

FIGS. 10a–c illustrate one embodiment of an inhalation device (a metered dose inhaler) having a microchip drug delivery device incorporated therein.

FIGS. 11a–d illustrate one embodiment of a fragrance delivery system.

DETAILED DESCRIPTION OF THE INVENTION

I. Delivery Apparatus and Systems

Figure 1:
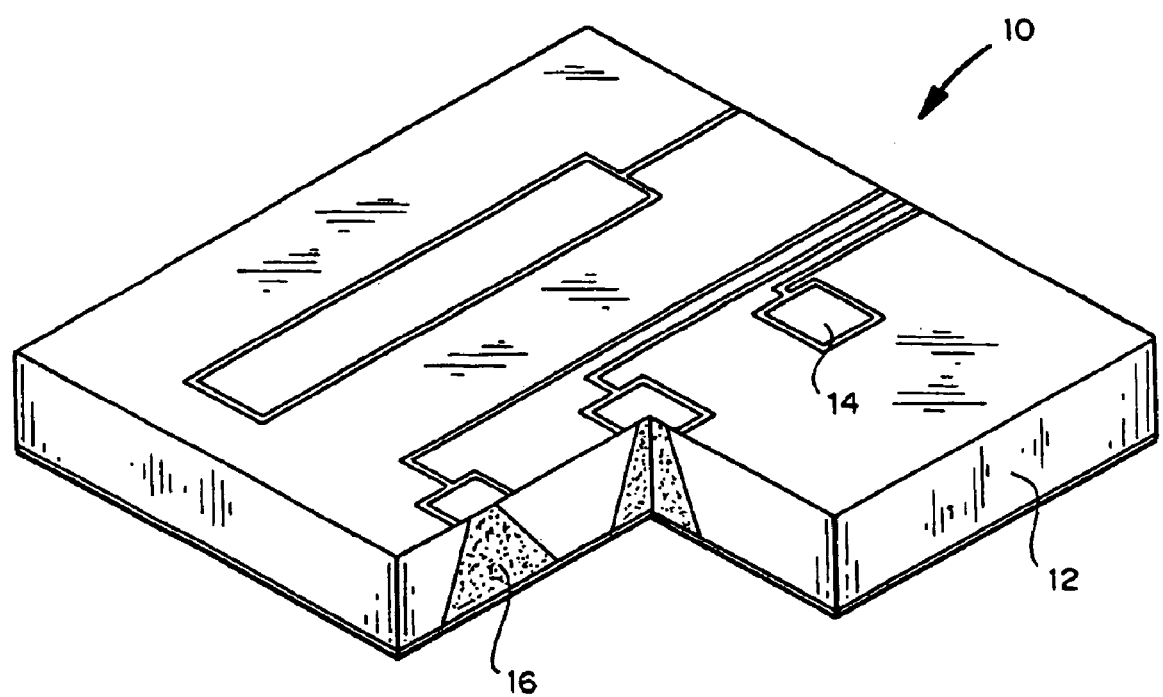
FIG. 1 is a perspective view of a typical microchip device for chemical delivery.

The delivery system includes one or more microchip devices, as described, for example, herein and in U.S. Pat. No. 5,797,898 and U.S. Pat. No. 6,123,861 to Santini et al., which are hereby incorporated by reference in their entirety. See, for example, FIG. 1, which illustrates a typical microchip device 10 with substrate 12, reservoirs 16, and reservoir caps 14. The microchip device is integrated with an apparatus providing active and passive release of molecules into a carrier fluid. The apparatus may include a quantity of the carrier fluid or the carrier fluid may be external to the apparatus.

A. Microchip Devices

The microchip devices typically include a substrate having a plurality of reservoirs containing a release system that includes the molecules to be released. The microchip devices in some embodiments further includes one or more reservoir caps covering the reservoir openings. The reservoir caps can be designed and formed from a material which is selectively permeable to the molecules, which disintegrates to release the molecules, which ruptures to release the molecules, or a combination thereof. Active release systems may further include control circuitry and a power source.

1. The Substrate

The substrate contains the etched, molded, or machined reservoirs and serves as the support for the microchip. Any material that can serve as a support, is suitable for etching, molding, or machining, and is impermeable to the molecules to be delivered and to the surrounding fluids, for example, water, organic solvents, blood, electrolytes or other solutions, may be used as a substrate. Examples of substrate materials include ceramics, semiconductors, and degradable and non-degradable polymers. For drug delivery applications outside of the body, such as drug release into a gaseous stream in an inhaler, it is preferred that the substrate itself is non-toxic, but it is not required. For in vivo applications such as stent drug delivery into vascular fluids, a sterile, biocompatible material is preferred. Nevertheless, toxic or otherwise non-biocompatible materials may be encapsulated in a biocompatible material, such as poly(ethylene glycol) or tetrafluoroethylene-like materials, before use.

For applications outside of drug delivery, such as diagnostics or fragrance delivery, substrate biocompatibility may be much less of an issue. One example of a strong, non-degradable, easily etched substrate that is impermeable to the molecules to be delivered and the surrounding fluids is silicon. An example of a class of strong, biocompatible materials are the poly(anhydride-co-imides) described in Uhrich et al., "Synthesis and characterization of degradable poly(anhydride-co-imides)", *Macromolecules*, 28:2184–93 (1995).

Figure 2A:
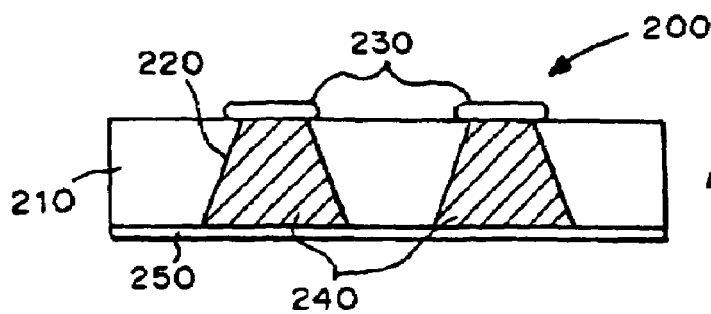
FIGS. 2a–e are cross-sectional schematic views of various embodiments of devices having substrates formed from two fabricated substrate portions which have been joined together.
Figure 2B:
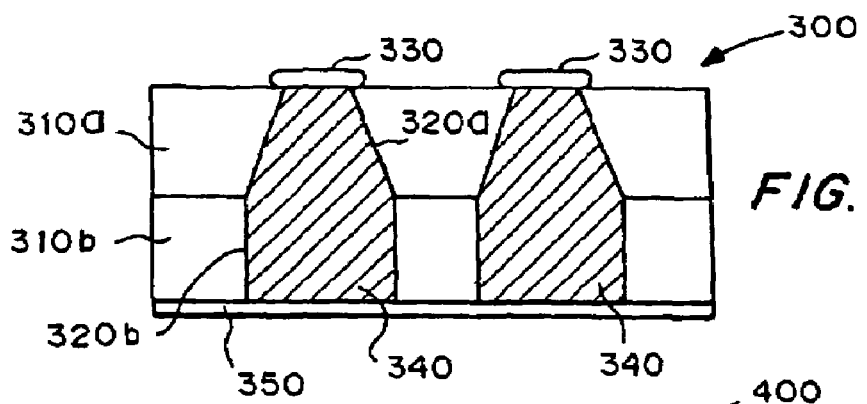
Figure 2C:
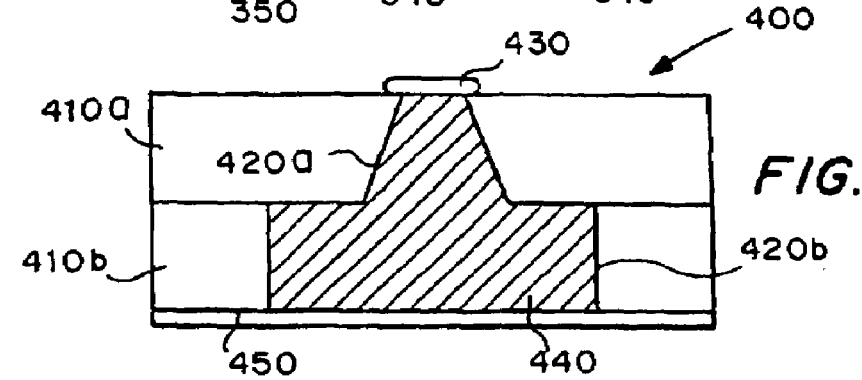
Figure 2D:
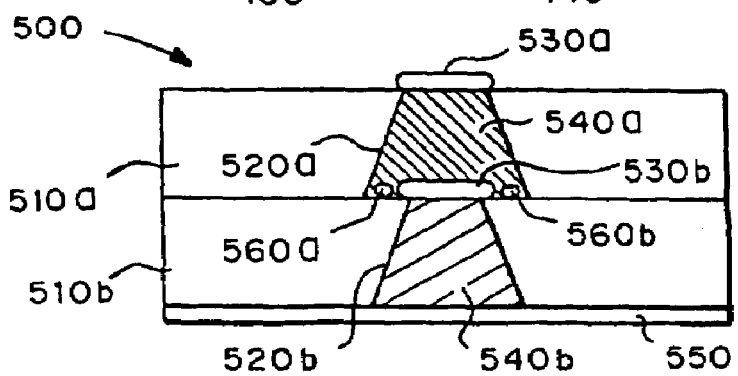
Figure 2E:
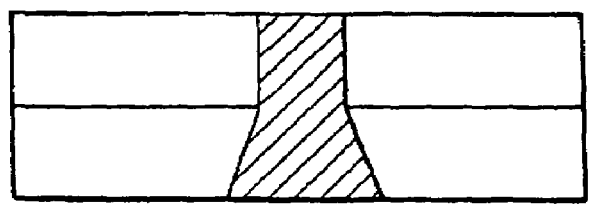

The substrate can be formed of only one material or can be a composite or multi-laminate material, e.g., several layers of the same or different substrate materials that are bonded together. Multi-portion substrates can include any number of layers of ceramics, semiconductors, metals, polymers, or other substrate materials. Two or more complete microchip devices also can be bonded together to form multi-portion substrate devices, as illustrated for example in FIGS. 2a–e. FIG. 2a, for comparison, shows a "single" substrate device 200, which has substrate 210, in which reservoirs 220 are filled with molecules to be released 240. Reservoirs 220 are covered by reservoir caps 230 and sealed with backing plate 250 or other type of seal. FIG. 2b shows device 300 having a substrate formed of a top substrate portion 310a bonded to bottom substrate portion 310b. Reservoirs 320a, in top substrate portion 310a are in communication with reservoirs 320b in bottom substrate portion 310b. Reservoirs 320a/320b are filled with molecules to be released 340 and are covered by reservoir caps 330 and sealed with backing plate 350 or other type of seal. FIG. 2c shows device 400 having a substrate formed of a top substrate portion 410a bonded to bottom substrate portion 410b. Top substrate portion 410a has reservoir 420a which is in communication with reservoir 420b in bottom substrate portion 410b. Reservoir 420b is much larger than reservoir 420a and reservoirs 420a/420b contain molecules to be released 440. Reservoirs 420a/420b are filled with molecules to be released 440 and are covered by reservoir cap 430 and sealed with backing plate 450 or other type of seal. FIG. 4d shows device 500 having a substrate formed of a top substrate portion 510a bonded to bottom substrate portion 510b. Top substrate portion 510a has reservoir 520a which contains first molecules to be released 540a. Bottom substrate portion 510b has reservoir 520b which contains second molecules to be released 540b. First molecules to be released 540a can be the same or different from second molecules to be released 540b. Reservoir 520a is covered by reservoir cap 530a and sealed by reservoir cap 530b (formed of an anode material) and partially by bottom substrate portion 510b. Reservoir 520b is covered by internal reservoir cap 530b and sealed with backing plate 550 or other type of seal. Cathodes 560a and 560b are positioned to form an electric potential with anode reservoir cap 530b. In one embodiment of the device shown in FIG. 2d, second molecules to be released 540b are first released from reservoir 520b, through or following the disintegration of reservoir cap 530b, into reservoir 520a, wherein the second molecules mix with first molecules to be released 540a before the mixture of molecules is released from reservoir 520a through or following the disintegration of reservoir cap 530a. FIG. 2e shows another reservoir shape configuration in cross-section. Substrate portions 310a/410a/510a can be formed from the same or different materials and can have the same or different thicknesses as substrate portions 310b/410b/510b. These substrate portions can be bonded or attached together after they have been individually processed (e.g., etched), or they may be formed before they have any reservoirs or other features etched or micromachined into them (such as in SOI substrates).

2. Release System

The molecules to be delivered may be inserted into the reservoirs in their pure form, as a liquid solution or gel, or they may be encapsulated within or by a release system. As used herein, "release system" includes both the situation where the molecules are in pure form, as either a solid or liquid, or are in a matrix formed of degradable material or a material which releases incorporated molecules by diffusion out of or disintegration of the matrix. The molecules can be sometimes contained in a release system because the degradation, dissolution, or diffusion properties of the release system provide a method for controlling the release rate of the molecules. The molecules can be homogeneously or heterogeneously distributed within the release system. Selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems typically are preferred due to the better characterization of release profiles.

The release system is selected based on the period over which release is desired. In the case of applications outside of the body, the release times may range from a fraction of a second to several months. In contrast, release times for in vivo applications, such as stent drug delivery, generally are within the range of several minutes to a year. In some cases, continuous (constant) release from a reservoir may be most useful. In other cases, a pulse (bulk) release from a reservoir may provide more effective results. A single pulse from one reservoir can be transformed into pulsatile release by using multiple reservoirs. It is also possible to incorporate several layers of a release system and other materials into a single reservoir to achieve pulsatile delivery from a single reservoir. Continuous release can be achieved by incorporating a release system that degrades, dissolves, or allows diffusion of molecules through it over an extended period of time. In addition, continuous release can be simulated by releasing several pulses of molecules in quick succession.

The release system material can be selected so that molecules of various molecular weights are released from a reservoir by diffusion out of or through the material or by degradation of the material. In one embodiment for the technology outside of the body, the degradation or disintegration of the release system may occur by increasing its equilibrium vapor pressure causing the release system to evaporate, thereby releasing the molecules. This can be achieved by actively increasing the temperature of the release system with thin film resistors or passively through chemical interactions with the carrier liquids and/or gases. In the case of in vivo applications, it may be preferred that biodegradable polymers, bioerodible hydrogels, and protein delivery systems are used for the release of molecules by diffusion, degradation, or dissolution. In general, these materials degrade or dissolve either by enzymatic hydrolysis or exposure to water, or by surface or bulk erosion. Representative synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include: poly(ethers) such as poly(ethylene oxide), poly(ethylene glycol), and poly(tetramethylene oxide); vinyl polymers-poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof.

3. Reservoir Caps (i) Passive Release by Disintegration or Diusion

In the passive timed release drug delivery devices, the reservoir caps are formed from a material that degrades or dissolves over time, or does not degrade or dissolve, but is permeable to the molecules to be delivered. These materials are preferably polymeric materials. Materials can be selected for use as reservoir caps to give a variety of degradation rates, dissolution rates, or permeabilities to enable the release of molecules from different reservoirs at different times and, in some cases, different rates. To obtain different release times (amounts of release time delay), caps can be formed of different polymers, the same polymer with different degrees of crosslinking, or a UV polymerizable polymer. In the latter case, varying the exposure of this polymer to UV light results in varying degrees of crosslinking and gives the cap material different diffusion properties or degradation or dissolution rates. Another way to obtain different release times is by using one polymer, but varying the thickness of that polymer. Thicker films of some polymers result in delayed release time. Any combination of polymer, degree of crosslinking, or polymer thickness can be modified to obtain a specific release time or rate. In one embodiment, the release system containing the molecules to be delivered is covered by a degradable cap material that is nearly impermeable to the molecules. The time of release of the molecules from the reservoir will be limited by the time necessary for the cap material to degrade or dissolve. In another embodiment, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays the onset of release. If diffusion through the cap material is limiting, the cap material determines the release rate of the molecules in addition to delaying the onset of release.

(ii) Active Release by Disintegration

In one embodiment of the active timed-release devices, the reservoir caps consist of a thin film of conductive material that is deposited over the reservoir, patterned to a desired geometry, and serves as an anode. Cathodes are also fabricated on the device with their size and placement dependent on the device's application and method of electric potential control. The anode is defined as the electrode where oxidation occurs. Any conductive material capable of dissolving into solution or forming soluble ions or oxidation compounds upon application of an electric current or potential (electrochemical dissolution) can be used for the fabrication of the anodes and cathodes. In addition, materials that normally form insoluble ions or oxidation products in response to an electric potential can be used if, for example, local pH changes near the anode cause these oxidation products to become soluble. Examples of suitable reservoir cap materials include metals such as copper, gold, silver, and zinc, and some polymers, as described, for example, in Kwon et al., "Electrically erodible polymer gel for controlled release of drugs", *Nature*, 354:291–93 (1991); and Bae et al., "Pulsatile drug release by electric stimulus", *ACS Symposium Series*, 545: 98–110 (1994).

(iii) Release by Rupture

In another embodiment, the reservoir cap is positioned on the reservoir over the molecules, which are released from the reservoir upon heating or cooling the device, or a portion thereof, to rupture the reservoir cap. As used herein, the term "rupture" includes fracture or some other form of mechanical failure, as well as a loss of structural integrity due to a phase change, e.g., melting, in response to a change in temperature, unless a specific one of these mechanisms is indicated.

In a preferred embodiment, heating or cooling causes the molecules in the reservoir to thermally expand (i.e. increase in volume). At a given temperature (T1), the release system completely fills the volume of the reservoir. Upon heating to temperature T2, the release system begins to expand and applies a force on the reservoir cap. Once this force exceeds the fracture strength of the cap, the reservoir cap fractures and the molecules are released. In a variation of this embodiment, the molecules can vaporize or undergo a reaction, thereby elevating the pressure within the reservoir sufficiently to cause the reservoir cap to rupture due to the mechanical stress. Prior to the application of heat, the pressure within the reservoir is lower than that needed to rupture the reservoir cap. The addition of heat increases the equilibrium pressure within the reservoir and the forces acting on the cap material increase. Further increases in temperature cause the pressure to continue to increase until the internal pressure overcomes the fracture strength of the reservoir cap. Typically the thermal expansion, vaporization, or reaction is induced by heating the molecules in the reservoir, e.g. above ambient temperatures. In certain applications, however, the thermal expansion or reaction can be induced by cooling the molecules in the reservoir. Water, for example, expands upon freezing. If a material that thermally contracts upon cooling is used as the reservoir cap over aqueous molecules, then the mechanical failure should be further enhanced by sufficient cooling.

In one embodiment, the reservoir cap is ruptured by physical (i.e. structural) or chemical changes in the reservoir cap material itself, for example, a change caused by a temperature change. For example, the reservoir cap can be made of or include a material that expands when heated. When the reservoir cap is secured in a fixed position and heated, the reservoir cap expands until it cracks or ruptures due to the increase in volume. This embodiment permits heating of the reservoir cap with minimal or no heating of the reservoir contents, a feature that is particularly important when the reservoir contains heat-sensitive molecules, such as protein drugs, which can denature upon exposure to excessive heat.

In another embodiment using an active release mechanism, the reservoir cap material is melted (i.e., undergoes a phase change) using resistive heating. For in vivo applications, the reservoir cap preferably is composed of biocompatible copolymers, such as organic hydroxy acid derivatives (e.g., lactides and lactones), which can offer a range of selectable melting temperatures (see PCT WO 98/26814). Particular melting temperatures, for example between about 2° C. and about 12° C. above normal body temperature, can be selected for the reservoir caps by proper selection of starting monomer ratios and the resulting molecular weight of the copolymer. This type of reservoir opening mechanism offers at least two delivery schemes. A first scheme is based on individual reservoir caps having various melting temperatures. By heating the device, or portion thereof, to a constant temperature, only specific reservoir caps melt, opening the reservoir and exposing the molecules. The application of different temperature profiles therefore provides for the selective molecular release. A second scheme, shown in FIG. 13, focuses on all caps having a fixed composition and a uniform melting temperature. The cap is a solid phase at temperature T1. Locally heating individual reservoir caps to temperature T2 causes the reservoir cap to become molten. The fluidized reservoir cap is then mobile, which facilitates the opening of the reservoir and release of molecules. In the case of in vitro applications, similar active schemes are possible with less stringent compositional and temperature requirements.

In the passive release embodiments, reservoir cap rupture is triggered by environmental temperature changes, for example, due to the placement of the device onto or into the body of a human or other animal. The passive mechanism differs from the active mechanism in that rupture of the reservoir cap of the active device is triggered by a directly applied temperature change rather than an environmental one.

In one embodiment of passive devices, the reservoir cap is thermally stimulated to enhance degradation. For example, the kinetics of reservoir cap degradation can be very slow at room temperature and the cap can be considered chemically stable. However, the kinetics of degradation are significantly increased by increasing the temperature of the cap material, e.g., by in vivo implantation. The absolute rate of degradation can be selected by controlling the composition of the reservoir cap material. For example, the degradation rate of biocompatible copolymers (e.g., lactones and lactides) can be between several hours and several years, preferably between two days and one year at a temperature of 37° C., depending on the specific molar ratios of the primary structural units. By using an array of reservoir caps, each having a different composition, complex molecular release profiles can be achieved once the device reaches a critical temperature defined by its environment.

In another embodiment of passive devices, all reservoir caps have constant disintegration rates (e.g., temperature independent) and the release profile is controlled by selection of the physical dimensions of the reservoir cap material. By fixing the rate of disintegration, the time for cap disintegration is dependent on the thickness of the reservoir cap material. For example, in an embodiment in which all reservoir caps have identical compositions, molecular release can be controlled by varying the thickness of the cap.

In both the active and passive devices, the reservoir cap is formed of a material having a yield or tensile strength beyond which the material fails by fracture or a material that undergoes a phase change (e.g., melts) with selected changes in temperature. The material preferably is selected from metals, such as copper, gold, silver, platinum, and zinc; glasses; ceramics; semiconductors; and brittle polymers, such as semicrystalline polyesters. Preferably the reservoir cap is in the form of a thin film, e.g., a film having a thickness between about 0.1 μm and 1 μm. However, because the thickness depends on the particular material and the mechanism of rupture (i.e., electrochemical vs. mechanical breakdown), thicker reservoir caps, e.g., having a thickness between 1 μm and 100 μm or more, may work better for some materials, such as certain brittle materials.

The reservoir cap optionally can be coated with an overcoat material to structurally reinforce the rupturable material layer until the overcoat material has been substantially removed by dissolving, eroding, biodegrading, oxidizing, or otherwise degrading, such as upon exposure to water in vivo or in vitro. Representative suitable degradable materials include synthetic or natural biodegradable polymers.

Reservoir caps in either passive or active embodiments can be formed of a material that functions as a permeable or semi-permeable membrane depending on the temperature.

In one preferred embodiment of the active release device, a resistor is integrated into the reservoir or mounted near the reservoir, which upon application of an electric current through the resistor, heats the contents of the reservoir, the cap material, or both. In typical embodiments, resistors are located at the bottom or along the inside walls of the reservoirs, or they may be located on or near the reservoir caps covering the small reservoir openings. The resistor generally is a thin-film resistor, which can be integrated with the reservoir during the manufacturing process. Such resistors can be made of metals such as platinum or gold, ceramics, semiconductors, and some polymers. Methods for fabricating these resistors are described, for example, in Wogersien et al. "Fabrication of Thin Film Resistors and Silicon Microstructures Using a Frequency Doubled Nd:YAG-Laser," *Proc. SPIE-Int. Soc. Opt. Eng.*, 3680: 1105–12 (1999); Bhattacharya & Tummala, "Next Generation Integral Passives: Materials, Processes, and Integration of Resistors and Capacitors on PWB Substrates," *J. Mater. Sci.-Mater. Electron.* 11(3):253–68 (2000); and Vladimirsky et al., "Thin Metal Film Thermal Micro-Sensors," *Proc. SPIE-Int. Soc. Opt. Eng.*, 2640:184–92 (1995). Alternatively, small chip resistors can be surface mounted on the device in close proximity to the reservoir or reservoir cap.

4. Molecules to be Delivered

Any natural or synthetic, organic or inorganic molecule or mixture thereof can be delivered. In one embodiment, the microchip is used to deliver drugs systemically to a patient by releasing the drugs into a fluid delivered intravenously. As used herein, the term "drug" includes therapeutic, prophylactic, and diagnostic agents, unless otherwise indicated. Drug molecules to be released during intravenous drug delivery applications include, but are not limited to, antibiotics, chemotherapeutic agents, in vivo diagnostic agents (e.g., contrast agents), sugars, vitamins, toxin antidotes, anti-inflammatory agents, painkillers, and medications useful for renal procedures such as dialysis (e.g., heparin). In another embodiment, the microchip releases molecules into a fluid stream for therapeutic or aesthetic purposes. For example, the molecules to be released into liquid or gaseous fluids may include, but are not limited to, aromatherapy hydrosols, various fragrances, colorants, and artificial and natural sweeteners. The field of analytical chemistry represents yet another embodiment in which a small (milligram to nanogram) amount of one or more molecules is required. Effective example molecules are pH buffering agents, diagnostic agents, and reagents in complex reactions such as the polymerase chain reaction or other nucleic acid amplification procedures.

One embodiment for in vivo molecular release is stent drug delivery into vascular fluids. Possible molecules to be released include anti-restinosis compounds, proteins, nucleic acids, polysaccharides and synthetic organic molecules, having a bioactive effect, for example, anesthetics, vaccines, chemotherapeutic agents, hormones, painkillers, metabolites, sugars, immunomodulators, antioxidants, ion channel regulators, and antibiotics. The drugs can be in the form of a single drug or drug mixtures and can include pharmaceutically acceptable carriers.

B. Other System or Apparatus Components

The delivery system or apparatus for releasing molecules into a carrier fluid can further include a variety of other components depending on the particular application.

1. Mixing Chambers, Mixers, and Pumps

In a preferred embodiment for some applications, such as in the intravenous (IV) drug administration system described below, the system further includes a mixing chamber in which the carrier fluid and released drug are combined. As used herein, unless otherwise indicated, a "mixing chamber" can be essentially any structure in which a carrier fluid can be temporarily contained, e.g., through which the carrier fluid can flow, while the molecules from the microchip device can contact the carrier fluid. A mixing chamber can be located adjacent the microchip device or downstream in a system in which the carrier fluid flows past a surface of the microchip device from which molecules are released. The carrier fluid and the drug mix locally by diffusion driven by concentration gradients or due to the reduction in the chemical potential of the fluid.

To speed the mixing process, a mixer (i.e., mixing device) optionally may be incorporated into the mixing chamber of the apparatus in order to use turbulence or convective transport to ensure a homogenous mixture. Dynamic and static mixers suitable for use in these devices are known in the art.

Carrier fluid can be provided at one or more surfaces of the microchip device in a static or flowing manner. Flow can be produced, for example, by gravity, capillary action, or through the use of one or more pumps. For embodiments utilizing a pump, the pump can be located separate from the apparatus or can be provided in the apparatus or system, for example in the mixing chamber. Pumps suitable for use in these devices are known in the art. See, e.g., U.S. Pat. No. 5,709,534 to O'Leary and U.S. Pat. No. 5,056,992 to Simons. In some embodiments, a pump can produce sufficient turbulence to mix the drug and carrier fluid, such that a separate mixer is not needed.

In the IV application described herein, the drug solution can enter the patient by gravity feed methods or alternatively one or more pumps can be integrated with the apparatus to pump the solution into the patient.

2. Stents

In one embodiment, the microchip device is incorporated into a stent. Stents are currently used in a range of medical applications, normally to prevent reocclusion of a vessel. Examples include cardiovascular and gastroenterology stents. Generally these stents are non-degradable. Ureteric and urethral stents are used to relieve obstruction in a variety of benign, malignant and post-traumatic conditions such as the presence of stones and/or stone fragments, or other ureteral obstructions such as those associated with ureteral stricture, carcinoma of abdominal organs, retroperitoneal fibrosis or ureteral trauma, or in association with Extracorporeal Shock Wave Lithotripsy. The stent may be placed using endoscopic surgical techniques or percutaneously. Examples of state of the art stents include the double pigtail ureteral stent (C. R. Bard, Inc., Covington, Ga.), SpiraStent (Urosurge, Coralville, Iowa), and the Cook Urological Ureteral and Urethral Stents (Cook Urological, Spencer, Ind.).

Bioabsorbable stents are particularly desirable in applications such as urological applications, since a second procedure is not required to remove the stent. Furthermore, one of the main problems in using metallic stents in cardiovascular applications is the subsequent restenosis caused by excessive growth of the endothelial wall, which is believed due, at least in part, to irritation caused by the metallic stent on the vessel wall (see Behrend, *American J. Cardiol. p.* 45, TCT Abstracts (October 1998); Unverdorben, et al., *American J. Cardiol. p.* 46, TCT Abstracts (October 1998)). A bioabsorbable stent made from, or coated with appropriate materials should produce reduced or no irritation. Bioabsorbable stents can be fabricated using methods known in the art, for example the methods and procedures described in U.S. Pat. Nos. 5,792,106; 5,769,883; 5,766,710; 5,670,161; 5,629,077; 5,551,954; 5,500,013; 5,464,450; 5,443,458; 5,306,286; 5,059,211, and 5,085,629. See also Tanquay, *Cardiology Clinics,* 23:699–713 (1994), and Taija, *J. Endourology,* 11:391–97 (1997).

Integration of microchip devices into stents is described in further detail in the "Applications" section below.

II. Carrier Fluid

The molecules contained in the reservoirs of the microchip device can be released into a variety of carrier fluids, depending on the particular application. The carrier fluid can be essentially of any composition in a fluid form. As used herein, the term "fluid" includes, but is not limited to, liquids, gases, supercritical fluid, solutions, suspensions, gels, and pastes.

Representative examples of suitable carrier fluids for medical applications include natural biological fluids and other physiologically acceptably fluids such as water, saline solution, sugar solution, blood plasma, and whole blood, as well as oxygen, air, nitrogen, and inhalation propellants. The choice of carrier fluid depends on the particular medical application, for example, stent applications, intravenous delivery systems, implantable delivery systems, or systems for respiratory (e.g., pulmonary) administration.

Representative examples of suitable carrier fluids for use in fragrance release systems include water, organic solvents (such as ethanol or isopropyl alcohol), aqueous solutions, and mixtures of any of these.

Representative examples of suitable carrier fluids for use in beverage additive systems include beverages or beverage bases of any type, such as water (both carbonated and non-carbonated), sugar solutions, and solutions of artificial sweeteners.

Essentially any chemical fluid can be used as the carrier fluid in an analytical or diagnostic system, depending on the specific fluid being analyzed. Examples include, but are not limited to, environmental samples of air or water, industrial or laboratory process sampling analysis, fluid samples to be screened in quality control assessments for food, beverage, and drug manufacturing, and combinatorial screening fluids.

III. Operation and Molecule Release

Figure 3A:
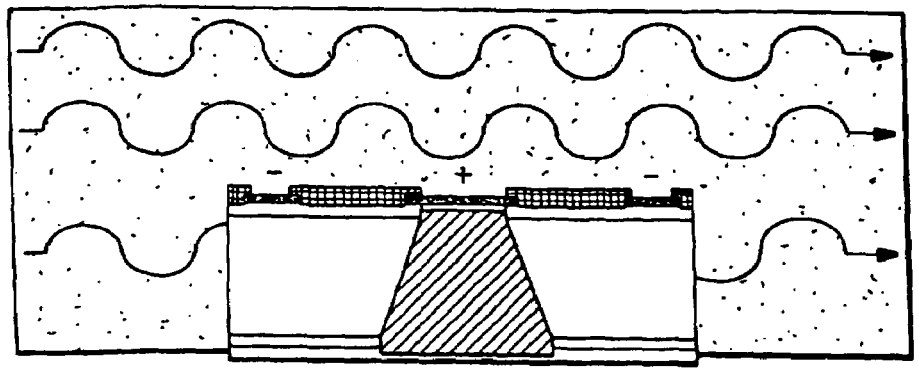
FIGS. 3a–c are cross-sectional views showing the active release of molecules from a microchip device into a carrier liquid.
Figure 3B:
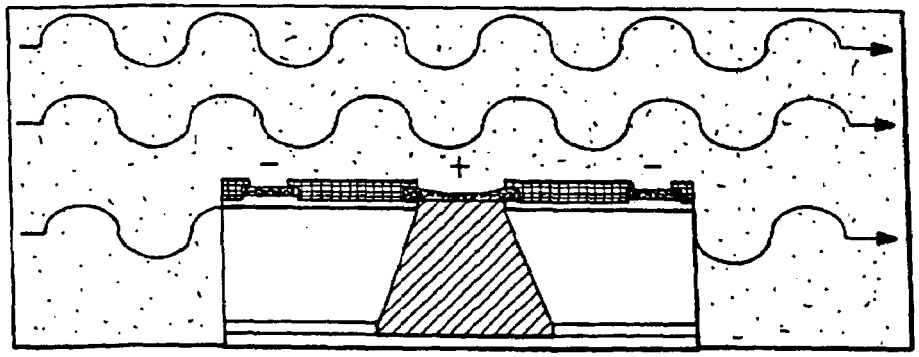
Figure 3C:
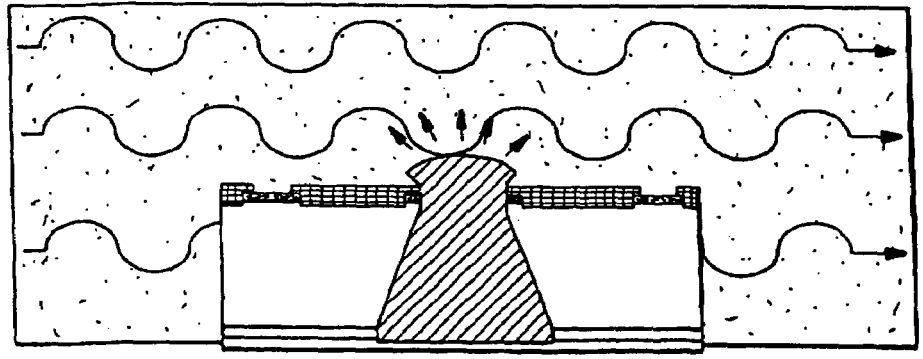

One preferred embodiment is the active release of molecules into a liquid carrier from a microchip that releases molecules in response to electrochemical stimulation, which is shown in FIG. 3. The application of an electrical potential (see FIG. 3*a*) causes the cap material to dissolve (see FIG. 3*b*) providing for the release of the molecules into the liquid flowing adjacent to the reservoir opening as shown in FIG. 3*c*. In a preferred embodiment, the electric current is modulated, rather than maintained at a constant value.

Another embodiment includes the release of the molecular species into a flowing gaseous phase (see FIGS. 4*a–c*). The application of heat to the release system can cause it to expand and apply pressure to the cap material (temperature T1<temperature T2). At some critical temperature and applied pressure, the cap will fracture exposing and releasing the molecules into the flowing gases that surround the device (temperature T2<temperature T3).

An alternative embodiment of an active release device uses the rupture of the membrane by a mechanical force as the release mechanism. See e.g., U.S. Pat. No. 5,167,625 to Jacobsen et al., which describes rupturing means that may be modified or adapted to the devices described herein. One non-limiting example is the rupturing of caps by forceful contact of the cap surface with an array of cantilevers that are fabricated using similar MEMS techniques or any other machining techniques (see FIG. 5). Ultrasonic waves are an alternative method capable of rupturing the cap material in order to expose the release system and release the molecules (see FIG. 6). Actuation of piezoelectric elements on or near the reservoir produces sonic waves that rupture the cap material. The piezoelectric elements can be composed of any material having crystal structure that is non-centrosymetric. Preferred piezoelectric materials are ceramics, such as $BaTiO_3$, $LiNbO_3$ and $ZnO$ (Chiang, Y., "*Physical Ceramics*", *John Wiley & Sons, Inc., New York,* pp. 37–66 (1997)), and polymers, such as polyvinylidene (Hunter & Lafontaine, "A Comparison of Muscle with Artificial Actuators," *Technical Digest of the* 1992 *Solid State Sensor and Actuator Workshop,* pp. 178–85 (1992)). These actuators can be fabricated in the form of thin films using standard techniques such as ion sputtering (Tjhen, et al., "Properties of Piezoelectric Thin Films for Micromechanical Devices and Systems," *Proceedings-IEEE Micro Electro Mechanical Systems, pp.* 114–19 (1991)) and sol-gel processing as described, for example, in Klein, "Sol-Gel Optics: Processing and Applications," *Kluwer Academic Publishers* 1994). The ultrasonic energy can be supplied by components located on the delivery device, in the carrier fluid, or outside of the delivery device. Methods for selecting which reservoirs are exposed include, for example, wave interference using secondary ultrasonic waves. The secondary waves can act to destructively interfere with the primary ultrasonic waves thus restricting the application of energy to only a selected set of reservoirs.

Additional embodiments involve the passive release of molecules into the carrier fluid. One general example of this application is the degradation of the release system when placed into or exposed to the carrier fluid. The chemical nature of the fluid, e.g., acid versus basic or polar versus non-polar, may cause the cap material to degrade or dissolve (see FIG. 6*b*). Once the cap material is completely dissolved, the molecules will be released into the liquid flowing adjacent to the reservoir opening (see FIG. 6*c*). The fluid can be any liquid or any gas that causes the disintegration of the release system or the cap material.

IV. Methods for Manufacture or Assembly

The microchip devices can be made, for example, using techniques known in the art, particularly the methods described in U.S. Pat. No. 6,123,861 to Santini et al., which is incorporated by reference. Although the fabrication methods described in the patent use microfabrication and microelectronic processing techniques, it is understood that fabrication of active and passive microchip chemical delivery devices is not limited to materials such as semiconductors or processes typically used in microelectronics manufacturing. For example, other materials, such as metals, ceramics, and polymers, can be used in the devices. Similarly, other fabrication processes, such as plating, casting, or molding, can also be used to make them.

In one embodiment, reservoirs also can be formed using silicon-oninsulator (SOI) techniques, such as is described in S. Renard, "Industrial MEMS on SOI," *J. Micromech. Microeng.* 10:245–249 (2000). SOI methods can be usefully adapted to form reservoirs having complex reservoir shapes, for example, as shown in FIGS. 2b, 2c, and 2e. SOI wafers behave essentially as two substrate portions that have been bonded on an atomic or molecular-scale before any reservoirs have been etched into either portion. SOI substrates easily allow the reservoirs (or reservoir sections) on either side of the insulator layer to be etched independently, enabling the reservoirs on either side of the insulator layer to have different shapes. The reservoir (portions) on either side of the insulator layer then can be connected to form a single reservoir having a complex geometry by removing the insulator layer between the two reservoirs using methods such as reactive ion etching, laser, ultrasound, or wet chemical etching.

The other system components are provided from known sources or can be easily fabricated or adapted from known devices and methods.

The microchip devices can be integrated into other system or device components (i.e. assembly of the system or apparatus) using techniques known in the art, such as by using adhesives and mechanical means such as fasteners, depending on the particular application.

IV. Applications

The microchip delivery systems can be used to release molecules into a variety of carrier fluids in a wide variety of forms. Representative examples include drug delivery into a fluid to be introduced or administered to a patient, such as intravenously or to the respiratory system; drug delivery from implanted systems including stents or micropumps; analytical or diagnostic chemistry; fragrance release systems; and beverage additive systems.

It is understood that the number, geometry, and placement of each reservoir, reservoir cap, or other object (e.g., resistors (heaters), electrodes, or channels) in or near each reservoir can be modified for a particular application. For simplicity, only one reservoir is shown in some Figures. However, it is understood that a microchip component or device would contain at least two, and preferably many more, reservoirs. Detailed below are some of the many useful applications.

A. Intravenous Drug Delivery System

An intravenous (IV) drug delivery system is provided that includes one or more microchip chemical delivery devices that release molecules into a physiologically acceptably carrier fluid for intravenous administration.

Figure 8A:
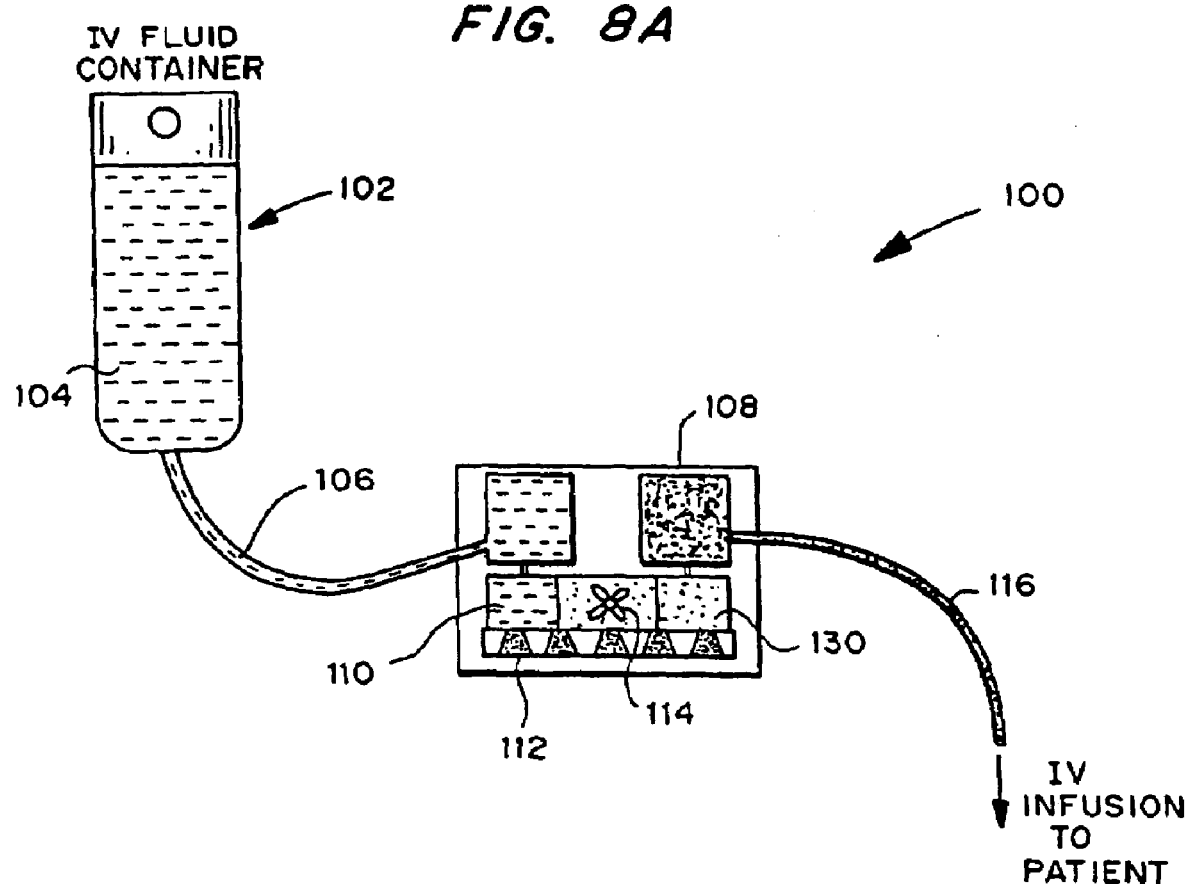
FIGS. 8a–b are cross-sectional views of two embodiments of intravenous drug delivery systems having integrated drug delivery microchips that release drug into a fluid delivered intravenously.

As illustrated in FIG. 8a, the IV system 100 includes console 108 which is connected to a catheter 106 extending from a container 102 (e.g., bag or bottle) of a carrier fluid 104. The carrier fluid flows from container 102 via catheter 106 (or other flexible hollow tubing) to console 108. In console 108, the carrier fluid 104 flows past one or more surfaces of the microchip device 112, mixes with released molecules in mixing chamber 130 using mixer 114 (optional) and then flows to the patient through a second catheter 116 (or other flexible hollow tubing) into the patient.

Figure 8B:
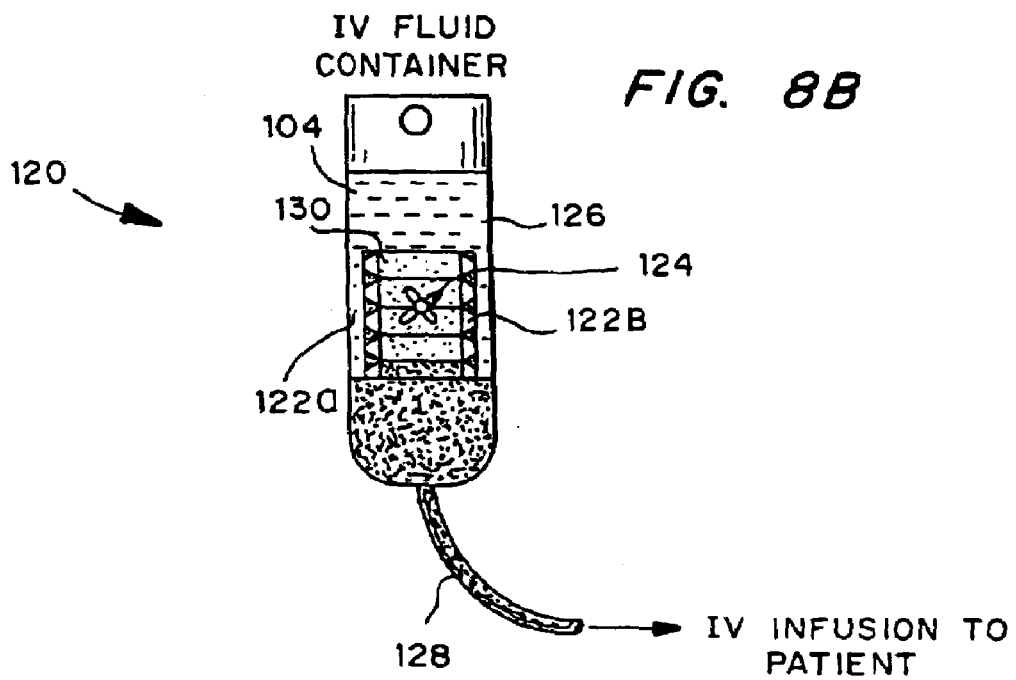

Another embodiment of the system is shown in FIG. 8b. This IV system 120 includes microchip devices 122a and 122b provided within container 126 of the carrier fluid 104. Carrier fluid 104 in mixing chamber 130 is mixed with released drug molecules using mixer 124 (optional). The resulting mixture flows from container 126, through tubing 128 to the patient. If an active microchip device is used in this way, the control electronics and power source preferably are integrated with the microchip device itself.

Figure 8C:
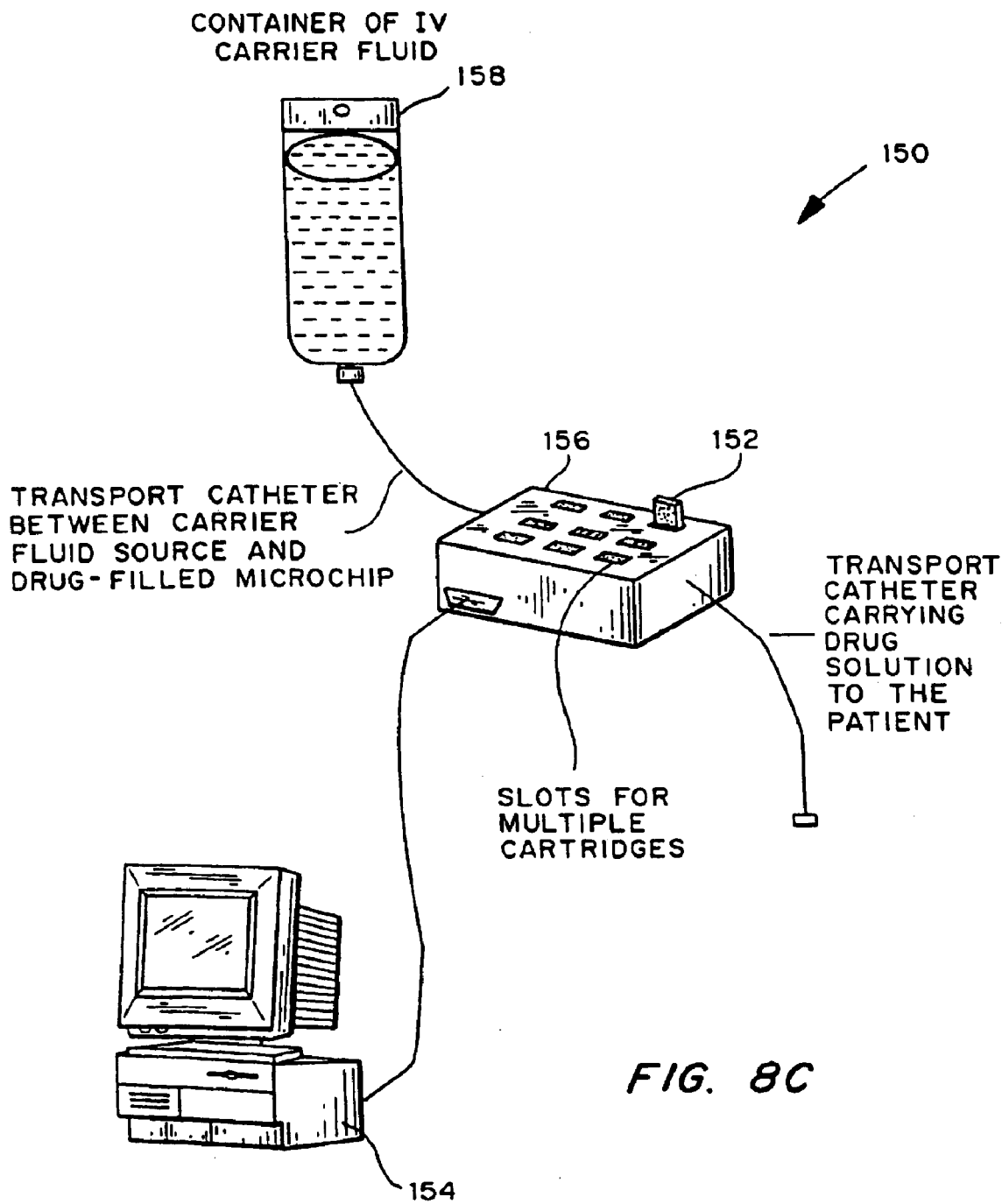
FIG. 8c is a perspective view of an intravenous drug delivery system including a multi-chambered interface console and a communications and digital control station.

In a preferred embodiment, shown in FIG. 8c, the IV system 150 includes a console 156 that contains "plug in" cartridges 152 comprising one or more drug-containing microchip devices, control electronics 154, and a container of IV carrier fluid 158.

In one embodiment, the IV system includes an electronic control system which can be programmed to send a signal to the microchip devices to release one or more drugs from one or more of the reservoirs of the microchip devices, thereby releasing the drugs into the carrier fluid as it passes by microchip devices and making a drug solution that is delivered into the patient. The electronic control systems can be connected to the console or to the microchip devices by cables or can transmit signals to the console or to the microchip devices by wireless communication means known in the art. Such an IV system may also include a digital readout that would display the critical drug delivery parameters such as the drug name, the release frequency, the release rate, the amount of drug left in the microchip, and the time at which the microchip will need to be replaced with a full one. The electronics also allow the physician to program in the type of release pattern desired, either pulsatile release or continuous release.

The inclusion of a microprocessor, memory, and a timer into the electronic control systems also can help decrease the potential for drug overdoses or the administration of the wrong drugs to patients. Safety protocols can be stored in the memory and continuously checked by the microprocessor to prohibit (i) the release of too much drug to a patient over a particular time interval, and/or (ii) the simultaneous release of two or more incompatible drugs. In addition, the microchip can store in memory the exact amount of drug delivered, its time of delivery, and the amount of drug remaining in the microchip. This information can be transmitted using wireless technology (e.g., for implants) or using standard computer connections (e.g., for external, in-line, or IV systems) to the physician or to a central monitoring system on a real-time basis. This allows the physician to remotely monitor the patient's condition.

One advantage provided by these embodiments is the ability to store drugs in the microchip in its most stable form (e.g., liquid, gel, or crystalline or powdered solid) until release into solution and delivery to the patient is desired. This can drastically increase the shelf-life (i.e. stability) of many drugs, particularly protein or biologic drugs, for which the stability is limited once dissolved in solution.

Another advantage is the reduction of medical errors. For example, numerous medical errors can result from traditional IV bags that are inadvertently filled with the incorrect amount of drug or bags that are mislabeled. Microchip "cartridges" as described herein can be labeled with a bar code indicating the type and amount of drug in the microchip. Once the microchip cartridge is plugged into the IV system or console, the IV system can detect the type and amount of drug and display it on the digital readout, which allows a physician or nurse to easily verify that the correct medication and dosage is delivered to the patient. It is understood that the microchip could also be placed at other locations between the carrier fluid container and the patient.

The body of the console preferably is made of a molded plastic. All parts in contact with the carrier fluid and/or the drug preferably are formed from or coated with a biocompatible material, preferably one, such as poly(tetrafluoroethylene) or a similar material, that does not interact with the fluids or released drugs. The mixing chamber and fluid connections should be leak-proof.

B. Drug Delivery Stent

Figure 9A:
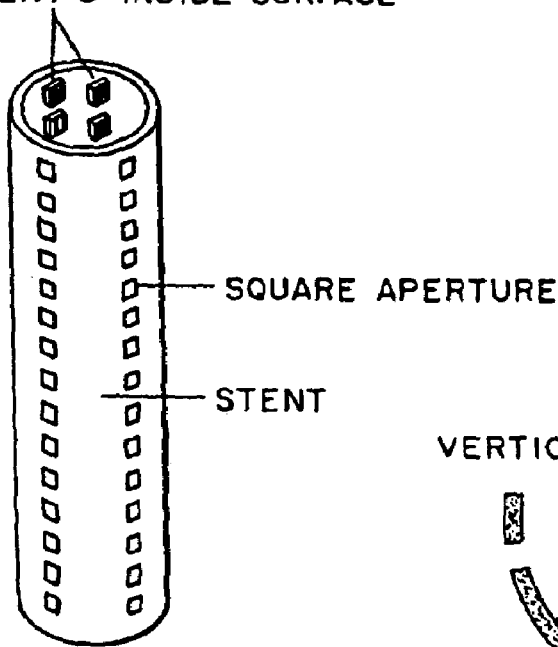
FIGS. 9a–c illustrate one embodiment of a stent-microchip drug delivery device, showing a perspective view (FIG. 9a), and two sectional views (FIGS. 9b and 9c).
Figure 9C:
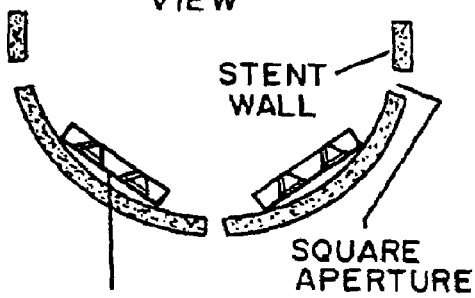
Figure 9B:
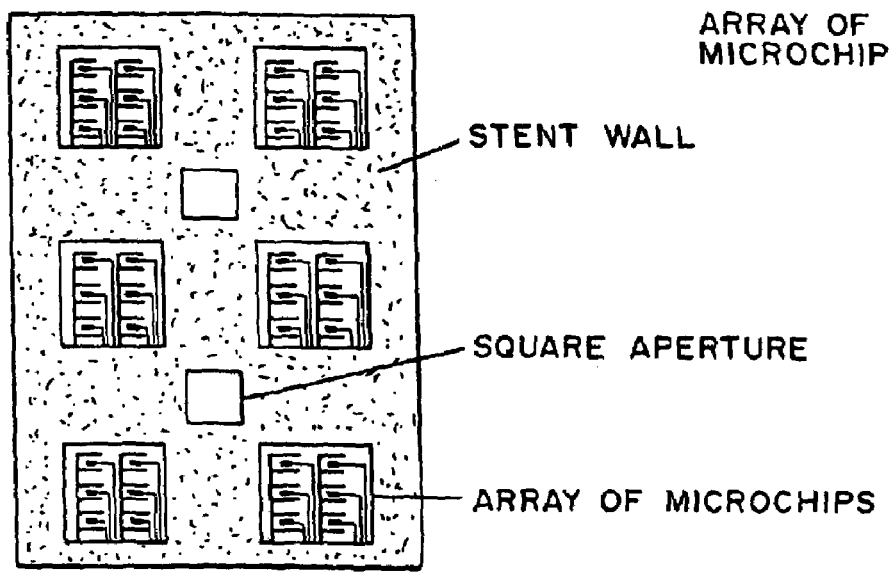
Figure 12:
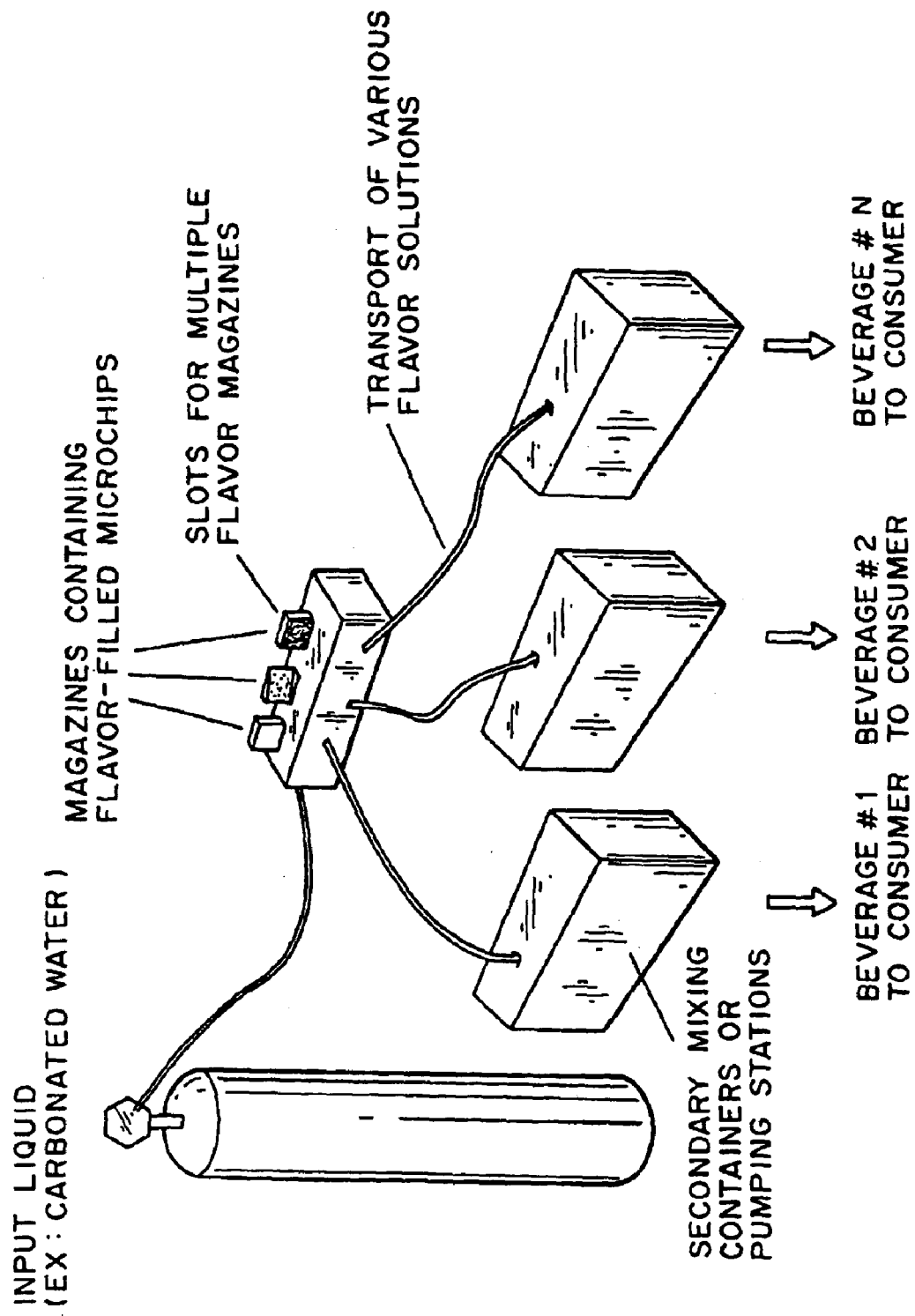
FIG. 12 illustrates one embodiment of a system for the introduction of additives to beverages.

One embodiment of a microchip device for the release of molecules into a carrier fluid involves integrating one or more drug delivery microchips into/onto a stent, such as a vascular stent. The drug-containing microchips preferably are provided on one or more surfaces of the stent, for example as illustrated in FIGS. 9a–c. The microchip devices can be present in the stent during implantation and stent expansion, or the microchip devices can be attached to the inside of the stent in a separate procedure immediately following stent implantation and expansion. If the microchips are small enough, implantation and attachment of a microchip to a stent can be completed using the same catheter technology used in the implantation of stents. In a preferred embodiment, the microchips of the stent-microchip device are programmed or activated by remote or wireless means to deliver drugs directly from the stent.

One preferred application of the stent-microchip device is the local delivery of anti-restenosis drugs to an artery that has recently undergone an angioplasty procedure. In another embodiment, the stent-microchip devices are used to systemically deliver one or more drugs to a patient via blood flowing through the stent. In another embodiment, stents can be designed and fabricated to have drug reservoirs and caps as part of the stent itself, that is, not as a separate microchip device, but rather as part of a monolithic stent device. It is understood that both systemic and local delivery of any drug is possible using the microchip technology in combination with stents.

The microchip-stent drug delivery devices are not limited to arterial and vascular applications. Microchips integrated with stenting technology can serve to deliver drugs within a variety of other channels in the body of humans and animals. Representative examples include the gastrointestinal tract, respiratory passages, reproductive and urinary tracts, renal vessels, cerebrospinal fluid passages, and sinuses.

C. Drug Inhalation Device

In another embodiment, microchip devices are used to release molecules into a gaseous carrier fluid, e.g., air, for subsequent inhalation by a patient. In one system, for example, a drug-containing microchip device is integrated into a metered dose inhaler (MDI) to provide a simple method for accurately controlling the molecular dose that is to be delivered. The microchip device also provides a controlled environment (within the reservoirs) that can function to extend the stability of the stored drug.

Many different styles of metered dose applicators appropriate for use with the drug-filled microchips are described in the art such as, for example, U.S. Pat. No. 6,116,234 to Genova et al. FIGS. 10a–c illustrate one embodiment of a schematic flow diagram of the drug delivery mechanism in a microchip metered dose inhaler. The drug-filled microchips are located on the inner wall of a replaceable cartridge on the open end of the applicator. Upon triggering an electrical signal from the power circuitry to the microchip(s) through a switch or timer, the doses can be released into a gas stream using various release techniques, such as the methods described in FIGS. 4–6. Once the reservoir cap has disintegrated or ruptured, a stream of gas flowing over the opened reservoir transports the drug molecules from the reservoirs to the patient. The carrier gas can be provided to the microchip device upon release of a pressurized gas or upon inhalation by the patient. The drug molecules can come out of reservoirs in the MDI by any of several mechanisms, including vaporization, formation of an aerosol, atomization, or by Bernoulli's principle. In an alternative embodiment, the molecules are released by diffusion or vaporization from the opened reservoirs into a static volume of the gas, which subsequently is inhaled by the patient, in a second step.

The dosage of the drug can be accurately measured by triggering release from a select number of reservoirs having a precise quantity of the drug. Each dosage can be composed of the molecules released by one or more reservoirs.

In preferred embodiments, the microchip-inhalation device advantageously provides reservoirs that are sealed until the patient activates the required molecular dose. Therefore, potentially harsh environments encountered during packaging, use, or storage will not affect the stability and concentration of each dose within the reservoir. The microchip devices can be contained, for example, within a replaceable cartridge located within the flow path of the carrier gas.

D. Diagnostic System

Microchips containing molecules for release into liquid and gaseous carrier fluids have a wide range of potential applications in diagnostics and analytical chemistry. In one embodiment of a diagnostic system, the microchip technology described herein can be integrated with a microfluidic array used in DNA testing, blood analysis, or testing of an environmental sample. In a preferred embodiment, a carrier fluid such as a saline solution is electrophoretically pumped through a tiny channel in a microfluidic array. Reservoirs containing reagent molecules and having active reservoir caps are located along the bottom of the microfluidic channels. As the saline solution is pumped into a channel containing the reagent filled reservoirs, a signal (e.g., an electric current) is sent to the reservoir caps to cause them to disintegrate, allowing the reagents inside the reservoirs to diffuse out into the saline solution in the channel. The release of reagents can occur while the fluid is stopped above the reservoirs or while the carrier fluid is flowing by the reservoirs. The saline solution containing the reagents is now pumped to a mixing chamber where the reagents are mixed with the sample of interest (e.g., a blood sample) and the desired interaction occurs.

Another example of a diagnostic system comes from combinatorial chemistry. Colloidal practices (e.g., the paint and coating industry) often necessitate the stabilization of suspensions which require a large array of experiments in search of an optimum chemistry. Chemicals such as surface-active catalysts, macromolecules and ionic salts, are just a few of the reagents used to determine the proper colloidal composition. Microchip devices filled with one or more of these colloidal additives can be placed in an agitated liquid medium containing the particulates. By disintegrating specific reservoir caps, for example by using a thermal activation technique, specific chemical species can be released in a controlled manner over time. This offers a method for accurately and automatically carrying out extensive combinatorial experiments.

Microchip devices also can be provided with integrated electrodes and circuitry that provide the means to characterize the stability of the colloid. Characterizations techniques such as ultrasound vibration potential (UVP) and electrokinetic sonic amplitude (ESA) are well known and have been described in detail by M. Rahaman in "Ceramics Processing and Sintering" (New York 1995). Therefore, the microchip device can provide information on both the chemistry required for stabilization and the stabilization kinetics. It is understood that the microchip device can serve in many other diagnostic and combinatorial applications such as DNA or genetic analyses, drug discovery, and environmental testing.

E. Microchip Device with Implantable Pump

In another embodiment, a microchip device is incorporated into an implantable micropumping system, for example for the delivery of drugs over extended periods of time, such as is needed the delivery of insulin to diabetics and treating certain kind of severe chronic pain. Micropump apparatus suitable for use in these devices are known in the art (see, e.g., U.S. Pat. No. 4,596,575 to Rosenberg). The micropump pumps the carrier fluid across one or more surfaces of the microchip device. A variety of carrier fluids can serve as the pumped fluid, including, but not limited to, filtered extra-cellular fluid, saline solution, or water.

In a preferred embodiment, release of doses is actively controlled, such as by disintegration of reservoir caps via electrochemical dissolution, as described in U.S. Pat. No. 5,797,898 and No. 6,123,861 to Santini. The release system preferably is in the form of a solid that is soluble in the carrier fluid. As the fluid passes over or around the activated and opened reservoir, the solid drug dissolves in the carrier fluid, forming a solution that is pumped into the extra-cellular environment.

F. Renal Applications

In renal dialysis procedures, the patient's blood flows through an ex vivo dialysis machine where toxic molecules are selectively removed from the blood, and the "cleaned" blood is returned to the patients body. These toxic molecules, which are normally removed from the blood by the kidneys, accumulate over time due to the decreased or improper functioning of the kidneys. While toxic molecules are removed from the patient's blood as it passes through the dialysis machine, therapeutic molecules and drugs can easily be added to the blood. This leads to a potential method for systemic delivery of multiple drugs or other molecules to a patient using a microchip device located ex vivo. In a preferred embodiment, microchip devices filled with drug molecules are placed in tubing through which blood flows during a dialysis procedure. The microchips can actively or passively delivery one or more types of molecules to the patients blood as it passes through the tubing. This method allows multiple drugs to be delivered accurately and directly into a patient's blood without having to implant the delivery device into the patient's body.

Modifications and variations of the methods and devices described herein will be obvious to those skilled in the art from the foregoing detailed description. Such modifications and variations are intended to come within the scope of the appended claims.

I claim:

1. An implantable device for controlled delivery of a drug comprising:
    a substrate;
    at least two reservoirs in the substrate, each reservoir having an opening;
    at least one therapeutic agent in each of the reservoirs;
    a reservoir cap sealing each opening;
    a mechanical rupturing mechanism which comprises a structure which moves, at the time selected for rupture of a reservoir cap, from a non-contacting position outside of the reservoir into contact with and ruptures the reservoir cap to permit release of the therapeutic agent from the reservoir through the opening; and
    a mixing chamber adjacent the reservoirs, wherein upon release of the therapeutic agent from at least one of the reservoirs, the therapeutic agent is combined with a carrier fluid in the mixing chamber and then transported to a delivery site in a human or animal.

2. The device of claim 1, wherein the mechanical rupturing mechanism comprises an array of cantilevers adapted to forcefully contact the surface of the reservoir cap to rupture the reservoir cap.

3. The device of claim 1, wherein the reservoir cap comprises a thin film formed of a metal, a polymer, or a combination thereof.

4. The device of claim 1, wherein the therapeutic agent is in a matrix formed of degradable material or a material which releases the therapeutic agent by diffusion out of or disintegration of the matrix.

5. The device of claim 4, wherein the matrix comprises a polymer is selected from the group consisting of polyamides, polyesters, polyanhydrides, polyorthoesters, and polycarbonates.

6. The device of claim 1, wherein the carrier fluid comprises a natural biological fluid.

7. The device of claim 1, wherein the therapeutic agent is transported to the delivery site by concentration gradient driven diffusion.

8. The device of claim 1, wherein the therapeutic agent is a protein.

9. The device of claim 1, wherein the therapeutic agent is a hormone.

10. The device of claim 1, wherein the therapeutic agent is a nucleic acid.

11. A method of delivering a drug to a human or animal patient in need thereof comprising:
    implanting in the patient a device which comprises a substrate, at least two reservoirs in the substrate, each reservoir having an opening, at least one therapeutic agent in each of the reservoirs, a reservoir cap sealing each opening, and a mixing chamber adjacent the reservoirs; and
    activating a mechanical rupturing mechanism which comprises a structure which moves from a non-contacting position outside of the reservoir into contact with the reservoir cap, rupturing the reservoir cap to permit release of the therapeutic agent from the reservoir through the opening such that the therapeutic agent combines with a carrier fluid in the mixing chamber and then is transported to a delivery site in the patient.

12. The method of claim 11, wherein the cater fluid is a natural biological fluid and the therapeutic agent is transported to the delivery site by concentration gradient driven diffusion.

13. The method of claim 11, wherein the mechanical rupturing mechanism comprises an array of cantilevers adapted to forcefully contact the surface of the reservoir cap to rupture the reservoir cap.

14. The method of claim 11, wherein the reservoir cap comprises a thin film formed of a metal, a polymer) or a combination thereof.

* * * * *